(12) United States Patent
Randolph et al.

(10) Patent No.: US 7,538,198 B2
(45) Date of Patent: ***May 26, 2009

(54) METHODS FOR PROTEIN REFOLDING

(75) Inventors: Theodore W. Randolph, Niwot, CO (US); John F. Carpenter, Littleton, CO (US); Richard J. St. John, San Francisco, CA (US); Jonathan N. Webb, Zionsville, IN (US)

(73) Assignee: Barofold, Inc., Boulder, CO (US)

( * ) Notice: Subject to any disclaimer, the term of this patent is extended or adjusted under 35 U.S.C. 154(b) by 617 days.

This patent is subject to a terminal disclaimer.

(21) Appl. No.: 10/425,371

(22) Filed: Apr. 29, 2003

(65) Prior Publication Data

US 2004/0038333 A1    Feb. 26, 2004

Related U.S. Application Data

(63) Continuation of application No. PCT/US01/45728, filed on Oct. 31, 2001.

(60) Provisional application No. 60/244,808, filed on Oct. 31, 2000.

(51) Int. Cl.
  *C07K 1/02*    (2006.01)
  *C12N 9/00*    (2006.01)
(52) U.S. Cl. ..................................... 530/427; 435/183
(58) Field of Classification Search ................. 435/183; 530/427
  See application file for complete search history.

(56) References Cited

U.S. PATENT DOCUMENTS

| | | | |
|---|---|---|---|
| 4,234,620 A * | 11/1980 | Howard et al. | 426/656 |
| 4,652,630 A | 3/1987 | Bentle et al. | 530/344 |
| 4,659,568 A | 4/1987 | Heilman, Jr. | 424/231.1 |
| 4,677,196 A | 6/1987 | Rausch et al. | 530/412 |
| 4,766,224 A | 8/1988 | Rausch | 530/412 |
| 4,923,967 A | 5/1990 | Bobbitt et al. | 530/351 |
| 4,929,700 A | 5/1990 | Halenbeck et al. | 530/351 |
| 4,985,544 A | 1/1991 | Yokoo et al. | 530/399 |
| 5,023,323 A | 6/1991 | Ho | 530/399 |
| 5,064,943 A | 11/1991 | McCoy et al. | 530/399 |
| 5,077,392 A | 12/1991 | Rudolph et al. | 530/387.1 |
| 5,109,117 A | 4/1992 | Ho | 530/399 |
| 5,162,507 A | 11/1992 | Wolfe et al. | 530/412 |
| 5,288,462 A | 2/1994 | Carter et al. | |
| 5,410,026 A | 4/1995 | Chang et al. | 530/408 |
| 5,593,865 A | 1/1997 | Rudolph et al. | 435/69.1 |
| 5,605,691 A | 2/1997 | Carroll | 424/184.1 |
| 5,708,148 A | 1/1998 | Schmitz et al. | 530/402 |
| 5,714,371 A | 2/1998 | Ramanathan et al. | 435/219 |
| 5,728,804 A | 3/1998 | Sharma et al. | 530/350 |
| 6,489,450 B2 | 12/2002 | Randolph et al. | 530/427 |
| 6,635,469 B1 * | 10/2003 | Litt et al. | 435/287.1 |
| 7,064,192 B2 * | 6/2006 | Randolph et al. | 530/427 |
| 2003/0083475 A1 | 5/2003 | Randolph et al. | |
| 2005/0020818 A1 | 1/2005 | Robinson et al. | |
| 2006/0188970 A1 | 8/2006 | Randolph et al. | |

FOREIGN PATENT DOCUMENTS

| | | |
|---|---|---|
| WO | WO 00/02901 | 1/2000 |
| WO | WO-02/062827 A2 | 8/2002 |
| WO | WO-02/062827 A3 | 8/2002 |
| WO | WO-2008/033555 A2 | 3/2007 |
| WO | WO-2008/033555 A3 | 3/2007 |
| WO | WO-2007/062174 A2 | 5/2007 |
| WO | WO-2007/062174 A3 | 5/2007 |
| WO | WO-2008/033556 A2 | 3/2008 |
| WO | WO-2008/033556 A3 | 3/2008 |

OTHER PUBLICATIONS

Anfinsen, "Principals that govern the folding of protein chains," *Science*, 181(4096):223-230, 1973.
Bam et al., "Molten globule intermediate of recombinant human growth hormone: stabilization with surfactants," *Biotechnology Progress*, 12:801-809, 1996.
Bam et al., "Tween protects recombinant human growth hormone against agitation-induced damage via hydrophobic interactions," *Journal of Pharmaceutical Sciences*, 87(12):1554-1559, 1998.
Betts et al., "Mutational effects on inclusion body formation," In: *Advances in Protein Chemistry*, 50:243-264, Academic Press Inc., San Diego, 1997.
Boteva et al., "Dissociation equilibrium of human recombinant interferon gamma," *Biochemistry*, 35(47):14825-14830, 1996.
Bowden et al., "Structure and morphology of protein inclusion bodies in *Escherichia coli*," *Bio/Technology*, 9:725-730, 1991.
Carpenter et al., "Rational design of stable lyophilized protein formulations: some practical advice," *Pharmaceutical Research*, 14(8):969-975, 1997.

(Continued)

*Primary Examiner*—Sandra Saucier
*Assistant Examiner*—Susan Hanley
(74) *Attorney, Agent, or Firm*—Cooley Godward Kronish LLP

(57) ABSTRACT

The present invention discloses improved methods of disaggregating protein aggregates, and refolding denatured proteins, using high pressure. In particular, the present invention provides for the use of agitation, high temperature, "stepped" depressurization, dialysis and dilution under pressure to increase the speed and extent of aggregate dissolution and protein refolding.

42 Claims, 15 Drawing Sheets

OTHER PUBLICATIONS

Clark et al., "Inhibition of aggregation side reactions during in vitro protein folding," In: *Amyloid, Prions, and Other Protein Aggregates*, Academic Press Inc, San Diego, 217-236, 1999.

Clark et al., "Oxidative renaturation of hen egg-white lysozyme. Folding vs. aggregation," *Biotechnology Progress*, 14:47-54, 1998.

Da Poian et al., "Differences in pressure stability of the three components of cowpea mosaic virus: implications for virus assembly and disassembly," *Biochemistry*, 33:8339-8346, 1994.

Defaye et al., "Renaturation of metmyoglobin subjected to high isostatic pressure," *Food Chemistry*, 52:19-22, 1995.

DeLoskey et al., "Isolation and refolding of H-ras from inclusion bodies of *Escherichia coli*: refold procedure and comparison of refolded and soluble H-ras," *Archives of Biochemistry and Biophysics*, 311(1):72-78, 1994.

Dewa et al., "Compression refolding of cytochrome C," *Protein and Peptide Letters*, 5(5):265-268, 1998.

Ealick et al., "3-dimensional structure of recombinant human interferon-gamma," *Science*, 252(5006):698-702, 1991.

Fink, "Protein aggregation: folding aggregates, inclusion bodies and amyloid," *Folding & Design*, 3(1):R9-R23, 1998.

Fischer et al., "A novel sequential procedure to enhance the renaturation of recombinant protein from *Escherichia coli* inclusion bodies," *Protein Engineering*, 5(6):593-596, 1992.

Fischer, In: *Lysozymes: Model Enzymes in Biochemistry and Biology*, Jolles (ed.), Birkhauser-Verlag, Boston, 143-161, 1996.

Foguel et al., "Hydrostatic pressure rescues native protein from aggregates," *Biotechnology and Bioengineering*, 63(5):552-558, 1999.

Goldberg et al., "A kinetic study of the competition between renaturation and aggregation during the refolding of denatured-reduced egg white lysozyme," *Biochemistry*, 30:2790-2797, 1991.

Goldenberg and Creighton, "Energetics of protein structure and folding," *Biopolymers*, 24:167-182, 1985.

Gorovits and Horowitz, "High hydrostatic pressure can reverse aggregation of protein folding intermediates and facilitate acquisition of native structure," *Biochemistry*, 37:6132-6135, 1998.

Gorovits et al., "High hydrostatic pressure induces the dissociation of cpn60 tetradecamers and reveals a plasticity of monomers," *The Journal of Biological Chemistry*, 270(5):2061-2066, 1995.

Gross and Jaenicke,, "Proteins under pressure—the influence of high hydrostatic-pressure on structure, function and assembly of proteins and protein complexes," *European Journal of Biochemistry*, 221(2):617-630, 1994.

Heremans and Smeller, "Protein structure and dynamics at high pressure," *Biochimica et Biophysica Acta*, 1386:353-370, 1998.

Hevehan and Clark, "Oxidative renaturation of lysozyme at high concentrations," *Biotechnology and Bioengineering*, 54:221-230, 1997.

Jaenicke and Koberstein, "High pressure dissociation of lactic dehydrogenase," *FEBS Letters*, 17(2):351-354, 1971.

Kendrick et al., "A transient expansion of the native state precedes aggregation of recombinant human interferon-gamma," *Proc. Natl. Acad. Sci., USA*, 95(24):14142-14146, 1998.

Komblatt et al., "The pressure-induced, reversible inactivation of mouse brain enolases," *Eur. J. Biochem.*, 128:577-581, 1982.

Lange et al., "Pressure induced protein structural changes as sensed by $4^{th}$ derivative UV spectroscopy," *Progress in Biotechnology*, 13:135-140, 1996.

Leach and Scheraga, "Effect of light scattering on ultraviolet difference spectra," *Journal of the American Chemical Society*, 82:4790-4792, 1960.

Maachupalli-Reddy et al., "Effect of inclusion body contaminants on the oxidative renaturation of hen egg white lysozyme," *Biotechnology Progress*, 13-144, vol. 150, 1997.

Maeda et al., "Effective renaturation of denatured and reduced immunoglobulin G in vitro without assistance of chaperone," *Protein Engineering*, 9(1):95-100, 1996.

Mitraki and King, "Protein folding intermediates and inclusion body formation," *Bio/Technology*, 7:690-697, 1989.

Mitraki et al., "Quasi-irreversibility in the unfolding-refolding transition of phosphoglycerate kinase induced by guanidine hydrochloride," *European Journal of Biochemistry*, 163:29-34, 1987.

Moore and Leppert, "Role of aggregated human growth hormone (hGH) in development of antibodies to hGH," *Journal of Clinical Endocrinology and Metabolism*, 51(4):691-697, 1980.

Müller et al., "Thermodynamics and mechanism of high-pressure deactivation and dissociation of porcine lactic dehydrogenase," *Biophysical Chemistry*, 16:1-7, 1982.

Oberg et al., "Nativelike secondary structure in interleukin-1β inclusion bodies by attenuated total reflectance FTIR," *Biochemistry*, 33:2628-2634, 1994.

Onuchic et al., "Theory of protein folding," *Ann. Rev. Phys. Chem.*, 48:545-600, 1997.

Paladini and Weber, "Pressure-induced reversible dissociation of enolase," *Biochemistry*, 20:2587-2593, 1981.

Panick et al., "Structural characterization of the pressure-denatured state and unfolding/refolding kinetics of staphylococcal nuclease by synchrotron small-angle X-ray scattering and Fourier-transform infrared spectroscopy," *J. Mol. Biol.*, 275:389-402, 1998.

Przybycien et al., "Secondary structure characterization of β-lactamase inclusion bodies," *Protein Engineering*, 7(1):131-136, 1994.

Ratner et al., "Persistent cutaneous insulin allergy resulting from high-moleuclar-weight insulin aggregates," *Diabetes*, 39:728-733, 1990.

Rietveld et al., "Deterministic pressure dissociation and unfolding of triose phosphate isomerase: persistent heterogeneity of a protein dimer," *Biochemistry*, 35:7743-7751, 1996.

Ruan and Weber, "Dissociation of yeast hexokinase by hydrostatic pressure," *Biochemistry*, 27:3295-3301, 1988.

Rudolph and Lilie, "In vitro folding of inclusion body proteins," *The FASEB Journal*, 10:49-56, 1996.

Rudolph, "Renaturation of recombinant, disulfide-bonded proteins form 'inclusion bodies'," In: *Modern Methods in Protein and Nucleic Acid Research*, Tschesche (ed.),149-171, 1990.

Shortle, "The denatured state (the other half of the folding equation) and its role in protein stability," *FASEB*, 10:27-34, 1996.

Silva and Weber, "Pressure stability of proteins," *Annual Review of Physical Chemistry*, 44:89-113, 1993.

Silva et al., "10. Pressure and cold denaturation of proteins, protein-DNA complexes, and viruses," In: *High-Pressure Effects in Molecular Biophysics and Enzymology*, Markley et al. (eds.), Oxford University.Press, pp. 133-148, 1996.

Silva et al., "Anomalous pressure dissociation of large protein aggregates—lack of concentration-dependence and irreversibility at extreme degrees of dissociation of extracellular hemoglobin," *J. Biol. Chem.*, 264(27):15863-15868, 1989.

Smeller et al., "Pressure effect on the temperature-induced unfolding and tendency to aggregate of myoglobin," *Biochemistry*, 38:3816-3820, 1999.

Spolar et al., "Coupling of local folding to site-specific binding of proteins to DNA," *Science*, 263:777-784, 1994.

St. John et al., "High pressure fosters protein refolding from aggregates at high concentrations," *Proc. Natl. Acad. Sci., USA*, 96(23):13029-13033, 1999.

International Search Report mailed Nov. 5, 1999 for PCT Application No. PCT/US99/15419, two pages.

International Search Report mailed Feb. 20, 2003 for PCT Application No. PCT/US01/45728, four pages.

Cleland, J.L. (1993). "Impact of Protein Folding on Biotechnology," Chapter 1 in *American Chemical Society* 526:1-21.

De Bernardez-Clark, E. et al. (1991). "Inclusion Bodies and Recovery of Proteins from the Aggregated State," Chapter 1 in *American Chemical Society* 470:1-20.

DeCordt, S. et al. (1997). "High Pressure Application in Food Preservation and Processing," *High Pressure Research in the Biosciences and Biotechnology*. K. Heremans ed., Leuven University Press:Leuven, Belgium, pp. 311-314.

Foguel, D. et al. (1998). "Characterization of a Partially Folded Monomer of the DNA-Binding Domain of Human Papillomavirus E2 Protein Obtained at High Pressure," *J Biol Chem.* 273(15):9050-9057.

Gorovits, B.M. et al. (1998). "Rhodanese Folding is Controlled By the Partitioning of its Folding Intermediates," *Biochim Biophys Acta.* 1382(1):120-128.

Jurkiewicz, E. et al. (1995). "Inactivation of Simian Immunodeficiency Virus by Hydrostatic Pressure," *Proc Natl Acad Sci U S A.* 92(15):6935-6937.

Patterson, M.F. et al. (1997). "Effect of High Hydrostatic Pressure on the Survival and Growth of *Escherichia coli* 0157:H7," *High Pressure Food Science, Bioscience, and Chemistry.* N.S. Isaacs ed., University of Reading, U.K. pp. 387-393.

Pontes, L. et al. (1997). "Pressure Inactivation of Animal Viruses: Potential Biotechnological Applications," *High Pressure Research in the Biosciences and Biotechnology.*K. Heremans ed., Leuven University Press:Leuven, Belgium, pp. 91-94.

Robinson, C.R. et al. (1995). "Hydrostatic and Osmotic Pressure as Tools to Study Macromolecular Recognition," *Methods Enzymol.* 259:395-427.

Lefebvre, B. et al. (Apr. 7, 2000). "Engineering Approaches to Reversing Protein Aggregation," Oral Presentation, *Mid-Atlantic Biochemical Engineering Consortium (MABEC) 13th Annual Meeting.* University of Delaware: Newark, DE. 4 pages.

Danek, B.L. (Apr. 7, 2000). "Poster Presentation 13: The Role of Cysteines and Disulfide Bonds in the Protein Folding of P22 Tailspike," *Mid-Atlantic Biochemical Engineering Consortium (MABEC) 13th Annual Meeting.* University of Delaware: Newark, DE. 3 pages.

Robinson, A.S. (Jun. 1, 2000). "Career: Characterization, Inhibition, and Reversal of Protein Aggregation," Grant Application Abstract, 1 page.

Robinson, A.S. (Oct. 1, 1997). "Powre: Molecular Determinants and Inhibition of Protein Aggregation," Grant Application Abstract, 1 page.

Shigehisa, T. et al. (1991). "Effects of High Hydrostatic Pressure on Characteristics of Pork Slurries and Inactivation of Microorganisms Associated with Meat and Meat Products," *Int J Food Microbiol.* 12(2-3):207-216.

Silva, J. L. et al. (1992). "Effects of Hydrostatic Pressure on a Membrane-Enveloped Virus: High Immunogenicity of the Pressure-Inactivated Virus," *J Virol.* 66(4):2111-7.

Silva, J.L. et al. (1992). "Dissociation of a Native Dimer to a Molten Globule Monomer. Effects of Pressure and Dilution on the Association Equilibrium of Arc Repressor," *J Mol Biol.* 223(2):545-555.

Silva, J.L. et al. (1996). "The Use of Hydrostatic Pressure as a Tool to Study Viruses and Other Macromolecular Assemblages," *Curr Opin Struct Biol.* 6(2):166-175.

Smelt, J.P. et al. (1997). "Inactivation Kinetics of Microorganisms by High Pressure," *High Pressure Research in the Biosciences and Biotechnology.*K. Heremans ed., Leuven University Press:Leuven, Belgium, pp. 273-276.

Tauscher, B. (1995). "Pasteurization of Food by Hydrostatic High Pressure: Chemical Aspects," *Z Lebensm Unters Forsch.* 200(1):3-13.

Webb, J.N. et al. (2000). "Stability of Subtilisin and Lysozyme under High Hydrostatic Pressure," *Biotechnol Prog.* 16(4):630-636.

Ferrão-Gonzales, A.D. et al. (Jun. 6, 2000). "The Preaggregated State of an Amyloidogenic Protein: Hydrostatic Pressure Converts Native Transthyretin Into the Amyloidogenic State," *PNAS USA* 97(12):6445-6450.

Kendrick, B.S. et al. (Oct. 1997). "Preferential Exclusion of Sucrose From Recombinant Interleukin-1 Receptor Antagonist: Role in Restricted Conformational Mobility and Compaction of Native State," *PNAS USA* 94:11917-11922.

Masson, P. et al. (2001). "High-Pressure Biotechnology in Medicine and Pharmaceutical Science," *Journal of Biomedicine and Biotechnology* 1(2):85-88.

Panda, M et al. (Jan. 7, 2000). "Productive and Nonproductive Intermediates in the Folding of Denatured Rhodanese," *Journal of Biological Chemistry* 275(1):63-70.

St. John, R.J. et al. (Dec. 14, 2001). "High Pressure Refolding of Recombinant Human Growth Hormone from Insoluble Aggregates," *Journal of Biological Chemistry* 276(50):46856-46863.

Tang, G.-Q. et al. (1996). "Pressure-Induced Dissociation Of Beef Liver L-Glutamate Dehydrogenase," In *Progress in Biotechnology,* vol. 13, Hayashi, R. et al. eds., Elsevier, pp. 163-166.

Thornton, C.A. et al. (Feb. 1993). "Safety of Intravenous Immunoglobulin," *Archives of Neurology* 50:135-136.

Valax, P. et al. (1993) "Molecular Characterization Of β-Lactamase Inclusion Bodies Produced In *Escherichia coli*. 1. Composition," *Biotechnology Progress* 9:539-547.

Vandenbroeck, K. et al. (1993). "Refolding And Single-Step Purification Of Porcine Interferon-γ From *Escherichia coli* Inclusion Bodies," *European Journal of Biochemistry* 215:481-486.

Webb, J.N. et al. (Jun. 19, 2001). "Partial Molar Volume, Surface Area, and Hydration Changes for Equilibrium Unfolding and Formation of Aggregation Transition State: High-Pressure and Cosolute Studies on Recombinant Human IFN-γ," *PNAS* 98(13):7259-7264.

Weber, G. (1987). "Dissociation Of Oligomeric Proteins By Hydrostatic Pressure," In *High Pressure Chemistry and Biochemistry*, van Eldick, R. et al. eds., D. Reidel Publishing Company, pp. 401-420.

Yamaguchi, T. et al. (1996). "High Pressure NMR Study of Protein Unfolding," In *Progress in Biotechnology,* vol. 13, Hayashi, R. et al. eds., Elsevier, pp. 141-146.

Zong, Q et al. (1995). "High-Pressure-Assisted Reconstitution of Recombinant Chloroperoxidase," *Biochemistry* 34:12420-12425.

Baneyx, F. (1999). "Recombinant Protein Expression in *Escherichia coli*," *Curr. Op. Biotechnol.* 10:411-421.

Boven, K. et al. (2005). "Epoetin-Associated Pure Red Cell Aplasia in Patients with Chronic Kidney Disease: Solving the Mystery." *Nephrol. Dial. Transplant.* 20(Suppl 3):iii33-iii40.

Braun, A. et al. (1997). "Protein Aggregates Seem to Play a Key Role Among the Parameters Influencing the Antigenicity of Interferon Alpha (IFN-α) in Normal and Transgenic Mice," *Pharm. Res.* 14(10):1472-1478.

Chi, E.Y. et al. (2003). "Roles of Conformational Stability and Colloidal Stability in the Aggregation of Recombinant Human Granulocyte Colony-Stimulating Factor," *Protein Sci.* 12:903-913.

De Bernardez Clark, E. (2001). "Protein Refolding for Industrial Processes," *Curr. Op. Biotechnol.* 12:202-207.

Deisenhammer, F. et al. (2004). "Measurement of Neutralizing Antibodies to Interferon Beta in Patients with Multiple Sclerosis," *J. Neurol.* 251(Suppl. 2):ll/31-ll/39.

Dzwolak, W. (2006, e-published Jan. 9, 2006). "Tuning Amyloidogenic Conformations Through Cosolvents and Hydrostatic Pressure: When the Soft Matter Becomes Even Softer," *Biochim. Biophys. Acta* 1764:470-480.

Grudzielanek, S. et al. (2006, e-published Dec. 9, 2005). "Solvation-assisted Pressure Tuning of Insulin Fibrillation: From Novel Aggregation Pathways to Biotechnological Applications," *Journal of Molecular Biology* 356:497-509.

Hermeling, S. et al. (Jun. 2004). "Structure-Immunogenicity Relationships of Therapeutic Proteins," *Pharm. Res.* 21(6):897-903.

Hermeling, S. et al. (Jun. 2005). "Development of a Transgenic Mouse Model Immune Tolerant for Human Interferon Beta," *Pharm. Res.* 22(6):847-851.

Hermeling, S. et al. (May 2006). "Antibody Response to Aggregated Human Interferon Alpha2b in Wild-Type and Transgenic Immune Tolerant Mice Depends on Type and Level of Aggregation," *J. Pharm. Sci.* 95(5):1084-1096.

International Search Report mailed Aug. 29, 2008, for PCT Application No. PCT/US2007/020128 filed Sep. 17, 2007, five pages.

Kim, Y-S. et al. (Jan. 21, 2000). "Thermodynamic Modulation of Light Chain Amyloid Fibril Formation." *J. Biol. Chem.* 275(3):1570-1574.

Kim, Y-S. et al. (Jan. 12, 2001). "Countering Effects of Renal Solutes on Amyloid Fibril Formation by Immunoglobulin Light Chains," *J. Biol. Chem.* 276(2):1626-1633.

Kim, Y-S. et al. (Jul. 26, 2002). "Kinetics and Energetics of Assembly, Nucleation, and Growth of Aggregates and Fibrils for an Amyloidogenic Protein," *J. Biol. Chem.* 277(30):27240-27246.

Kim, Y-S. et al. (2006). "High-Pressure Studies on Protein Aggregates and Amyloid Fibrils," Chapter 13 In *Methods in Enzymology,* Cadenas, E. et al. eds., Academic Press: San Diego, CA, 413:237-253.

Leach, S.J. et al. (Sep. 20, 1960). "Effect of Light Scattering on Ultraviolet Difference Spectra," *J. Am. Chem. Soc.* 82(18):4790-4792.

Lefebvre, B.G. et al. (2004). "Pressure Dissociation Studies Provide Insight into Olgomerization Competence of Temperature-Sensitive Folding Mutants of P22 Tailspike," *Protein Sci.* 13:1538-1546.

Purohit, V.S. et al. (Feb. 2006). "Influence of Aggregation on Immunogenicity of Recombinant Human Factor VIII in Hemophilia A Mice," *J. Pharm. Sci.* 95(2):358-371.

Randolph, T.W. et al. (2002). "High Hydrostatic Pressure as a Tool to Study Protein Aggregation and Amyloidosis," *Biochim. Biophys. Acta* 1595:224-234.

Rosenberg, A.S. (Aug. 4, 2006). "Effects of Protein Aggregates: An Immunologic Perspective," *AAPS J.* 8(3):E501-E507.

Runkel, L. et al. (1998). "Structural and Functional Differences Between Glycosylated and Non-Glycosylated Forms of Human Interferon-β (IFN-β)," *Pharm. Res.* 15(4):641-649.

Schellekens, H. (Jun. 2002). "Bioequivalence and the Immunogenicity of Biopharmaceuticals," *Nat. Rev.* 1(6):457-462.

Schellekens, H. (2003). "Immunogenicity of Therapeutic Proteins," *Nephrol. Dial. Transplant* 18:1257-1259.

Schellekens, H. (2005). "Factors Influencing the Immunogenicity of Therapeutic Proteins," *Nephrol. Dial. Transplant.* 20(Suppl 6):vi3-vi9.

Schellekens, H. et al. (Jun. 2006). "Eprex-Associated Pure Red Cell Aplasia and Leachates, " *Nat. Biotechnol.* 24(6):613-614.

Schwarz, E. et al. (Jul./Aug. 1996). "The Effect of Molecular Chaperones on In Vivo and In Vitro Folding Processes," *Biol. Chem.* 377(7/8):411-416.

Seefeldt, M.B. (Dec. 2, 2004). *High Pressure Refolding of Protein Aggregates: Efficacy and Thermodynamics*, Doctoral Thesis, presented Dec. 2, 2004, Department of Chemical and Biological Engineering, University of Colorado, Boulder, CO, 244 pages.

Seefeldt, M.B. et al. (Sep. 2005, e-pub. Aug. 4, 2005). "High-pressure Studies of Aggregation of Recombinant Human Interleukin-1 Receptor Antagonist: Thermodynamics, Kinetics, and Application to Accelerated Formulation Studies," *Protein Sci.* 14:2258-2266.

Seefeldt, M.B. et al. (Oct. 1, 2007, e-pub. Mar. 2, 2007). "Specific Volume and Adiabatic Compressibility Measurements of Native and Aggregated Recombinant Human Interleukin-1 Receptor Antagonist: Density Differences Enable Pressure-Modulated Refolding," *Biotechnol. Bioeng.* 98(2):476-485.

\* cited by examiner

METHODS FOR PROTEIN REFOLDING

CROSS-REFERENCE TO RELATED APPLICATIONS

This application is a continuation of PCT/US01/45728, filed Oct. 31, 2001, which claims priority from U.S. Provisional Application Ser. No. 60/244,808, filed Oct. 31, 2000.

BACKGROUND OF THE INVENTION

1. Field of the Invention

The present invention relates generally to the field of protein biochemistry. More particularly, it concerns improved methods for the renaturation and refolding of polypeptides aggregates.

2. Description of Related Art

The aggregation of proteins is of significant concern in the biotechnology, pharmaceutical and medical communities. In vitro, aggregation is observed in virtually every step in the production, refolding, purification, storage and shipping of protein therapeutics (Carpenter et al., 1997; Clark et al., 1999). In vivo, numerous pathogenic conditions in humans (e.g., Alzheimer's disease, Parkinson's disease and prion diseases (Kelly, 1996; Kelly, 1998; Prusiner, 1998; Scherzinger et al., 1999)) have protein aggregation and formation of insoluble deposits associated with the condition and, as a result, research on the characterization of the aggregates and mechanisms of aggregation in these diseases is an active area of medical research.

Aggregation in human protein deposition diseases, which displays organization in the form of insoluble fibrils, has brought increased significance to the study of protein misassembly and aggregation processes in general (Wetzel, 1999). Investigation into the reversal of aggregation and precipitation processes has immediate practical implications for the production, purification and delivery of therapeutic proteins.

In the production of therapeutic proteins, aggregated precipitates (e.g., inclusion bodies) is commonly reversed by dissolution of the precipitated aggregates in the presence of high concentrations of chaotrope (e.g., 6 M guanidine hydrochloride). Such harsh conditions result both in disaggregation (solubilization) and in nearly complete unfolding of the protein. Commonly, refolding is effected by removal of the chaotrope via dialysis or dilution to protein concentrations of ca. 10 to 50 μg/mL (Clark et al., 1999). Because refolding is commonly a first-order (in protein concentration) process and aggregation a second-order or higher process, refolding yields are improved at lower protein concentrations (Clark et al., 1999). Soluble aggregates are often separated from the native protein by costly and time consuming column chromatographies. Separated soluble aggregates are typically discarded, thus reducing overall protein yields and substantially increasing protein production costs. An alternative to chaotropic dissolution to dissolve insoluble aggregates or column purification to remove soluble aggregates is disaggregation by pressure (Foguel et al., 1999; Gorovits & Horowitz 1998; St. John et al., 1999).

Several research groups have exploited the ability of pressure to dissociate native protein oligomers (Silva & Weber 1993). In addition, others have explored the use of pressure to disaggregate and refold proteins from soluble non-native protein aggregates (Foguel et al., 1999; Gorovits & Horowitz, 1998) and precipitated, insoluble non-native aggregates (St. John, et al., 1999). Gorovits and Horowitz 1998 used high pressure to inhibit formation of soluble aggregates in 3.9 M urea solutions of rhodanase, and to reverse the formation of soluble aggregates. However, Gorovits & Horwitz (1998) report that "pressure . . . is not able to reverse large aggregates." Treatment at 2.4 kbar for 90 minutes of soluble aggregates formed from P22 tailspike protein reduced aggregate levels from 41.1 to 17.6% (Foguel et al., 1999).

St. John et al. (1999) used high pressure to dissolve and recover native protein from large, insoluble aggregates at pressures on the order of 200 MPa, including aggregates formed as inclusion bodies. High yields at high protein concentrations of refolded, active human growth hormone, lysozyme and β-lactamase from insoluble, precipitated aggregates were achieved using non-denaturing concentrations of guanidine hydrochloride in combination with pressure or pressure in the absence of guanidine hydrochloride (St. John et al., 1999). In the specific case of insoluble aggregates of lysozyme containing non-native intermolecular covalent disulfide bonds that served to crosslink the insoluble precipitates, redox shuffling agents such as mixtures of reduced and oxidized glutathione were used in combination with high pressure and 0.8M guanidine HCl to afford high yields of folded, biologically active protein. In the specific case of aggregated and precipitated and aggregated human growth hormone, low levels of a chaotrope such as guanidine HCl were used to optimize recovery of soluble, native protein. In the specific case of B-lactamase inclusion bodies, addition of guanidine HCl did not increase yield of biologically active B-lactamase, but did result in higher solubilization of contaminating proteins.

Nonetheless, improved methods for the high-pressure dissociation of protein aggregates and refolding of solubilized proteins are desired.

SUMMARY OF THE INVENTION

Thus, in accordance with the present invention, improved methods for the use of high pressure in protein disaggregation and refolding are provided. In one embodiment, there is provided a method of producing biologically active disaggregated protein from protein aggregates comprising:

(i) providing a protein aggregate;

(ii) mixing said protein aggregate with a reducing agent in amount sufficient to reduce disulfide bonds therein;

(iii) subjecting the mixture of step (ii) to increased pressure, as compared to ambient pressure, whereby said protein aggregate dissolves;

(iv) dialyzing the mixture under pressure, whereby said reducing agent is removed and disulfide bonds reform; and (v) removing the dissolved protein from increased pressure, whereby said protein refolds such that biological activity is retained. The method may further comprise the step of agitating said protein aggregate and/or dissolved protein to enhance dissolution and/or refolding; or may further comprise the step of subjecting said protein aggregate, prior to refolding, to a temperature of about 30° C. to about 125° C. The method may optionally exclude a chaotropic agent. Suitable reducing agents include diothiothreitol, glutathione, dithioerythritol, or β-mercaptoethanol. The increased pressure may comprise about 500 atmospheres to about 10,000 atmospheres.

The steps (ii)-(v) may be performed in about 3 hours to about 12 hours, particular in about 6 hours. Steps (ii) and (iii) may be performed in the presence of a chaotropic agent, and said method may further comprise the step of removing said chaotropic agent. Suitable chaotropic agents include guanidine, guanidine sulfate, guanidine hydrochloride, urea, thiocyanate, sarcosyl, sodium dodecyl sulfate, or sodium octyl sulfate.

The protein aggregate may comprise inclusion bodies, soluble and insoluble precipitates, soluble non-native oligomers, gel, fibrils, films, filaments, protofibrils, amyloid deposits, plaques, or dispersed non-native intracellular oligomers. The protein aggregate also may be subjected to pressure at high concentration, for example, at a concentration is from about 5 to 20 mg/ml, or more particularly, about 10 mg/ml. The protein aggregate may then be diluted under pressure, for example, to about 1 mg/ml.

In another embodiment, there is provided a method of producing biologically active disaggregated protein from protein aggregates comprising:
(i) providing a protein aggregate;
(ii) subjecting the said protein aggregate to increased pressure, as compared to ambient pressure, and agitation, whereby said protein aggregate dissolves; and
(iii) removing the dissolved protein from increased pressure, whereby said protein refolds such that biological activity is retained. The method may further comprise the step of agitating the dissolved protein to enhance refolding. Agitation may be provided by ultrasound energy, mechanical stirring, shaking, or pumping through static devices. It may may further comprise subjecting said protein aggregate, prior to refolding, to a temperature of about 30° C. to about 80° C. Optionally, the method does not utilize a chaotropic agent. The increased pressure may comprise about 500 atmospheres to about 10,000 atmospheres.

The steps (ii)-(v) may be performed in about 3 hours to about 12 hours, particular in about 6 hours. Steps (ii) and (iii) may be performed in the presence of a chaotropic agent, and said method may further comprise the step of removing said chaotropic agent. Suitable chaotropic agents include guanidine, guanidine sulfate, guanidine hydrochloride, urea, thiocyanate, sarcosyl, sodium dodecyl sulfate, or sodium octyl sulfate.

The method may further comprising mixing said protein aggregate with a reducing agent in amount sufficient to reduce disulfide bonds therein; and further may comprise dialyzing said mixture under pressure, whereby said reducing agent is removed and disulfide bonds reform. The reducing agent may be removed by diafiltration or ultrafiltration, or it may be negated by addition of an oxidizing agent. Suitable reducing agent is diothiothreitol, glutathione, dithioerythritol, or β-mercaptoethanol.

The protein aggregate may comprise inclusion bodies, soluble and insoluble precipitates, soluble non-native oligomers, gel, fibrils, films, filaments, protofibrils, amyloid deposits, plaques, or dispersed non-native intracellular oligomers. The protein aggregate also may be subjected to pressure at high concentration, for example, at a concentration is from about 5 to 20 mg/ml, or more particularly, about 10 mg/ml. The protein aggregate may then be diluted under pressure, for example, to about 1 mg/ml.

In yet another embodiment, there is provided a method of producing biologically active disaggregated protein from protein aggregates comprising:
(i) providing a protein aggregate;
(ii) subjecting the said protein aggregate to increased pressure, as compared to ambient pressure, and high temperature of about 30° C. to about 125° C., whereby said protein aggregate dissolves; and
(iii) removing the dissolved protein from increased pressure and high temperature, whereby said protein refolds such that biological activity is retained. Optionally, the method does not include use of a chaotropic agent. The method may further comprise the step of agitating said protein aggregate and/or dissolved protein to enhance dissolution and/or refolding; or may further comprise mixing said protein aggregate with a reducing agent in amount sufficient to reduce disulfide bonds therein. The mixture may be dialyzed under pressure, whereby said reducing agent is removed and disulfide bonds reform. Alternatively, the reducing agent I removed by diafiltration or ultrafiltration, or negated by addition of an oxidizing agent. Suitable reducing agents include diothiothreitol, glutathione, dithioerythritol, or βmercaptoethanol. The increased pressure may comprise about 500 atmospheres to about 10,000 atmospheres.

The steps (ii)-(v) may be performed in about 3 hours to about 12 hours, in particular in about 6 hours. Steps (ii) and (iii) may be performed in the presence of a chaotropic agent, and said method may further comprise the step of removing said chaotropic agent. Suitable chaotropic agents include guanidine, guanidine sulfate, guanidine hydrochloride, urea, thiocyanate, sarcosyl, sodium dodecyl sulfate, or sodium octyl sulfate.

The protein aggregate may comprise inclusion bodies, soluble and insoluble precipitates, soluble non-native oligomers, gel, fibrils, films, filaments, protofibrils, amyloid deposits, plaques, or dispersed non-native intracellular oligomers. The protein aggregate also may be subjected to pressure at high concentration, for example, at a concentration is from about 5 to 20 mg/ml, or more particularly, about 10 mg/ml. The protein aggregate may then be diluted under pressure, for example, to about 1 mg/ml.

In still yet another embodiment, there is provided a method of producing biologically active disaggregated protein from protein aggregates comprising:
(i) providing a protein aggregate;
(ii) mixing said protein aggregate with a reducing agent in amount sufficient to reduce disulfide bonds therein;
(iii) subjecting the mixture of step (ii) to increased pressure, as compared to ambient pressure, high temperature of about 30° C. to about 125° C., and agitation, whereby said protein aggregate dissolves;
(iv) removing or neutralizing said reducing agent, whereby disulfide bonds reform; and
(v) removing the dissolved protein from increased pressure and high temperature, whereby said protein refolds such that biological activity is retained. Optionally, the method does not include use of a chaotropic agent. The method may further comprise dialyzing said mixture under pressure, whereby said reducing agent is removed and disulfide bonds reform; or the method may further comprise removing said reducing agent by diafiltration or ultrafiltration. Alternatively, the effect of said reducing agent is negated by addition of an oxidizing agent. Suitable reducing agents include diothiothreitol, glutathione, dithioerythritol, or β-mercaptoethanol. The increased pressure may comprise about 500 atmospheres to about 10,000 atmospheres.

Steps (ii)-(iii) may be performed in about 1 hour to about 12 hours, in particular, in about 6 hours. The protein aggregate may comprise inclusion bodies, soluble and insoluble precipitates, soluble non-native oligomers, gel, fibrils, films, filaments, protofibrils, amyloid deposits, plaques, or dispersed non-native intracellular oligomers. The protein aggregate also may be subjected to pressure at high concentration, for example, at a concentration is from about 5 to 20 mg/ml, or more particularly, about 10 mg/ml. The protein aggregate may then be diluted under pressure, for example, to about 1 mg/ml.

Steps (ii) and (iii) may be performed in the presence of a chaotropic agent, and said method further comprises the step of removing said chaotropic agent. Suitable chaotropic agents include guanidine, guanidine sulfate, guanidine hydrochloride, urea, thiocyanate, sarcosyl, sodium dodecyl sulfate, or sodium octyl sulfate.

In a further embodiment, there is provided a method of producing biologically active disaggregated protein from protein aggregates comprising:
  (i) providing a protein aggregate;
  (ii) subjecting the said protein aggregate to a first increased pressure, as compared to ambient pressure, whereby said protein aggregate dissolves;
  (iii) subjecting the dissolved protein to a second pressure that is less than said first increased pressure, but still increased pressure as compared to ambient pressure, and
  (iv) removing the dissolved protein from said second increased pressure, whereby said protein refolds such that biological activity is retained. The first increased pressure may be about 200 MPa to about 1000 MPa. The second increased pressure may be about 100 MPa. The method may further comprise agitation of the protein under pressure; or the method may further comprising subjecting said protein to high temperature, for example a high temperature of about 30° C. to about 125° C.

The method may further comprise mixing the protein aggregate, prior to increased pressure, with a reducing agent. The method may also comprise dialyzing said mixture under pressure, whereby said reducing agent is removed and disulfide bonds reform. Alternatively, the reducing agent is removed by diafiltration or ultrafiltration, or is negated by addition of an oxidizing agent. Reducing agents include diothiothreitol, glutathione, dithioerythritol, or β-mercaptoethanol.

The protein aggregate also may be subjected to pressure at high concentration, for example, at a concentration is from about 5 to 20 mg/ml, or more particularly, about 10 mg/ml. The protein aggregate may then be diluted under pressure, for example, to about 1 mg/ml.

Steps (ii)-(iv) may be performed in about 3 hours to about 12 hours, or more particularly, in about 6 hours. Optionally, the method excludes chaotropic agents. Steps (ii)-(iv) may be performed in the presence of a chaotropic agent, and said method would further comprise the step of removing said chaotropic agent. Suitable chaotropic agents include guanidine, guanidine sulfate, guanidine hydrochloride, urea, thiocyanate, sarcosyl, sodium dodecyl sulfate, or sodium octyl sulfate.

The protein aggregate may comprise a protein multimer, for example, a hetero-multimer or a homo-multimer. Multimers may be selected from the group consisting of a dimer, a trimer, a tetramer, a pentamer, a hexamer, a heptamer, an octamer and a nonamer. Examples of multimeric proteins include interferon-γ, hemoglobin, lactic acid dehydrogenase, antibodies and antibody fragments.

All of the preceding methods may be performed on soluble denatured protein as well.

In additional embodiments, there are provided:
  a method of rendering a protein aggregate susceptible to dissolution by chaotropes, detergents and/or increased temperature comprising subjecting said protein aggregate to high pressure in combination with one or more of chaotropes, detergents and/or increased temperature;
  a method increasing the shelf-life of a protein sample comprising the steps of removing soluble protein aggregates by applying high pressure, followed by depressurization;
  a method of screening a protein composition for refolding conditions comprising:
    (i) providing a protein composition in physically distinct replicate samples;
    (ii) subjecting said replicate samples to different conditions comprising high pressure and varying temperature, buffers of varying pH, buffers of varying salt concentration, varying protein concentration, varying reducing agent concentration, varying stabilizing agents, varying chaotropic agents, varying detergents, varying surfactants; and
    (iii) removing said replicate samples from high pressure; and
    (iv) assessing protein refolding;
  a method of inactivating virus in a sample containing an protein of interest comprising:
    (i) providing a sample containing a desired protein, said protein being in a native or non-native state;
    (ii) treating said sample to reduce or eliminate infectious virus particles therein; and
    (iii) subjecting said sample to a high pressure protein refolding procedure;
  and a method of producing biologically active disaggregated protein from protein aggregates comprising:
    (i) providing a protein aggregate;
    (ii) subjecting the mixture of step (i) to increased pressure, as compared to ambient pressure, high temperature of about 30° C. to about 125° C., and agitation, whereby said protein aggregate dissolves;
    (iii) altering the pH of the mixture of step (ii) by dialysis; and
    (iv) removing the dissolved protein from increased pressure and high temperature,
  whereby said protein refolds such that biological activity is retained.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A—Absorbance at 310 run versus time for guanidine hydrochloride-induced aggregates at 250 MPa in succinate buffer. The total rhIFN-γ concentration was 1.0 mg/mL and the guanidine hydrochloride concentration in solution was ca. 5 mM. The absorbance of native rhIFN-γ at 310 nm in the absence of aggregates is ca. 0.06 AU mL/cm mg (data not shown). FIG. 6B—The second derivative extremum (near 286 nm) height versus time at 100 MPa for rhIFN-γ (1 mg/mL) guanidine hydrochloride-induced (▲) and thermally-induced (□) aggregates dissociated at 250 MPa. Error bars of are 95% confidence intervals on the spectral height. Spectral heights for the pressure-dissociated form at 250 MPa (dashed line), native liquid control (solid line with X) and pressure-refolded after equilibration at 0.1 MPa (dotted line) are included on the plot for reference.

DESCRIPTION OF ILLUSTRATIVE EMBODIMENTS

I. The Present Invention

Figure 1:
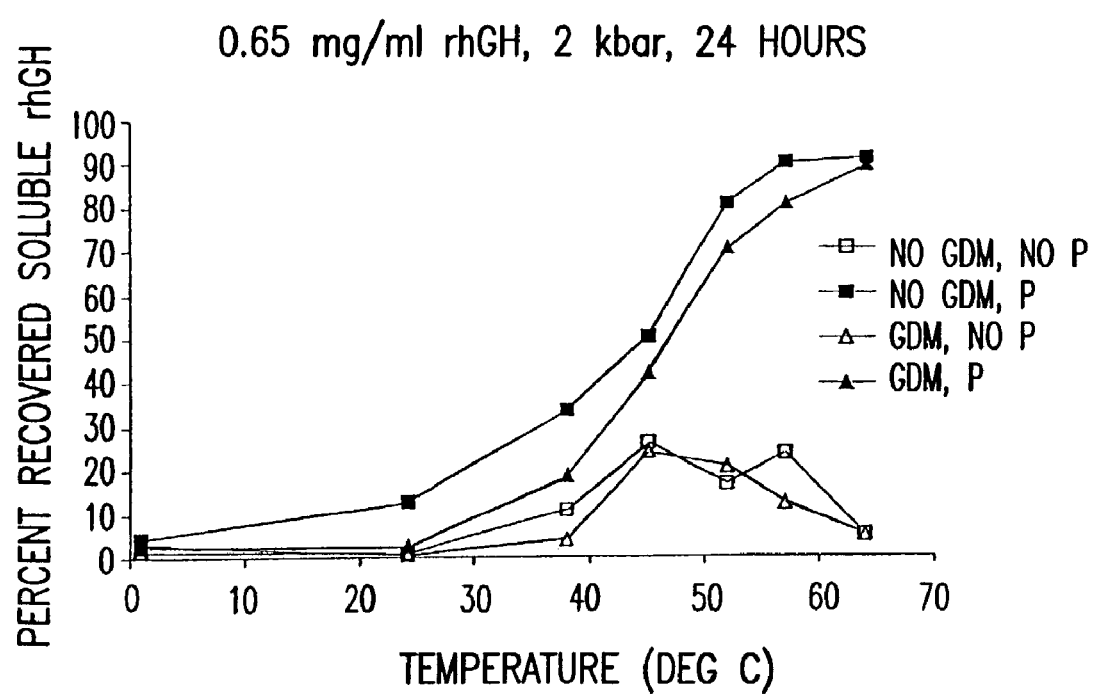
FIG. 1: High pressure recovery of rhGH aggregates in both buffer alone and 0.75M GdmHCl. Atmospheric standards are labeled with open symbols, while pressurized samples are labeled with solid symbols. Refolding buffers contain no GdmHCl.

Although not visible, soluble aggregates propose an extremely difficult and hazardous problem when producing protein products. Soluble aggregates decrease product values and, in the case of pharmaceutical preparations, can lead to dangerous anaphylactic reactions in patients that can be fatal. Many processing steps can cause formation of soluble aggregates, including: filtration, ultrafiltration, extraction, precipitation, crystallization, spray/freeze drying, concentration, and chromatography. Because filtration can cause additional formation of soluble aggregates, removal of these aggregates is extremely complex and difficult. In fact, commercially available protein products often are graded on the content of soluble aggregates in the formulation, and the value of a product can be drastically improved by a relatively small reduction in soluble aggregates (2-5%). Human serum albumin is an excellent example of a product whose value can be increased by reduction of aggregates.

Likewise, insoluble precipitates of non-native protein are often formed during the production, purification, packaging, storage, shipping and delivery of proteins. These aggregates are a human health hazard in the case of parentally-administered products, because the can provoke severe immune responses, including anaphylactic shock. Furthermore, synthesis of human proteins in recombinant cell cultures often results in the formation of insoluble precipitates of non-native, aggregated protein termed inclusion bodies. It should be noted that the inclusion bodies are often large enough to be viewed by transmission electron microscopy, and may contain covalent non-native intermolecular disulfide bonds. These inclusion bodies are typically processed by first dissolving them in high concentrations of chaotropic agents such as urea or guanidine, adding reducing agents to break disulfide bonds. After dissolution, the dissolved, unfolded protein is then typically diluted to concentrations below 1 mg/ml, and the urea or guanidine is slowly removed by diafiltration. Redox conditions are often specified at various times during the refolding process to allow native disulfide bonds to reform. The overall process requires large amounts of expensive reagents, equipment for handling large volumes of solutions and expensive waste disposal steps. In addition, the yields of properly folded, native protein are often less than 50%, and the desired protein is found in a dilute solution after refolding, requiring additional, expensive concentration steps after refolding is complete.

Previously, the inventors have described their work on the use of high pressure to facilitate disaggregation of insoluble protein aggregates, and to facilitate protein refolding. St. John et al. (1999), and in U.S. Ser. No. 09/350,327, by Randolph et al Combining hydrostatic pressure with low, non-denaturing concentrations of guanidine hydrochloride, human growth hormone aggregates were disaggregated and properly refolded protein was recovered at 100%. At 24° C. and in the absence of guanidine, recovery of native human growth hormone after pressure treatment at 2 kbar for 24 hours was only 20%.

In particular, U.S. Ser. No. 09/350,327 by Randolph et al. (incorporated by reference) provides effective methods for disaggregating and refolding of denatured, aggregated proteins in solution so that properly folded, biologically active protein in solution is recovered in high yield. Dissociation of protein aggregates takes place as the pressure is increased from about 0.25 kbar up to no more than about 12 kbar. The refolding takes place at pressures between about 0.25 kbar to about 3.5 kbar, advantageously at about 1.5 kbar to about 3 kbar. Typically a chaotropic agent is present at a concentration that is not effective for denaturing protein at atmospheric pressure, and sometimes is absent altogether. Optionally, oxidation-reduction reagents can be incorporated in the refolding solution so that native intramolecular disulfide bonds can be formed where that is desired. The method is applicable to substantially all proteins, especially for insoluble protein aggregates, inclusion bodies, or abnormal oligomeric (soluble) aggregates.

The present invention extends this work in the following ways:

- agitation of protein at various stages, in particular while the protein is under pressure, speeds and improves the disaggregation and refolding process;
- increasing the temperature during various incubations, including while the protein is undergoing disaggregation and refolding, also speeds the process and improves the yield, particularly in the absence of a chaotrope;
- removing or neutralizing the reducing agent while under pressure;
- dilution of protein to working concentration immediately after pressurization, which permits smaller volumes for high-pressure refolding equipment, which provides a substantial cost savings; and
- using intermediate pressures during refolding to permit intramolecular and intermolecular interactions to be "sorted" independently Using these elements in combination with the previously disclosed methods, either individually or in combination with one another, the present inventors provide improved methods of protein dissagregation and refolding under pressure, including significant time savings. The following paragraphs describe various embodiments of the present invention.

Augmenting conventional refolding processes; transition steps. In many refolding processes, there are critical steps at which certain reagents or conditions are removed or negated. These steps provide opportunities for refolded proteins to either unfold or aggregate and precipitate. In order to prevent this from occurring, one may utilize the present invention to "bridge" one treatment condition to the next. For example, removal of a detergent or chaotropic agent, or reduction of temperature, which are critical for further processing of a protein sample, creates a risk of aggregation. By subjecting samples to increased pressure while transitioning to a detergent or chaotrope free solution, or to room temperature, one reduces the chance of precipitation.

Similarly, some reagents or conditions, which are insufficient in and of themselves to facilitate disaggregation and/or refolding of proteins, can be augmented by the use of high pressure. While certain uses prosper by the exclusion of chaotropes or detergents, other uses may not be affected by these relatively harsh treatments. By using these reagents or conditions in conjunction with high pressure, it is possible to improve their performance and, in some cases, create an operable refolding process. Such combinations include pressure+increased temperature, pressure+detergent, pressure+chaotrope, etc.

Screening of folding conditions for gene products. Protein production can be facilitated by genetically modifying an appropriate host cell so as to cause it to produce a known or unknown proteinaceous product, using techniques well known to those skilled in the art. See Sambrook et al (1989). Unfortunately, these products often are found within the host cell as insoluble precipitates, and there may be considerable difficulty in recovering properly folded proteins from these precipitates. However, since each protein host cell combination is unique, it often takes laborious empirical experimentation to determine the appropriate refolding conditions.

In one aspect of the invention, homogenized samples of cell "paste" containing insoluble precipitates of a desired proteinaceous product, or partially purified preparations (e.g., by centrifugation to remove cell debris, followed by washing of the precipitate with buffered solutions containing surfactants to remove lipids) can be screened for optimal dissolution and folding conditions by placing them in individual sample containers. To these containers are also added aqueous solutions which may contain various buffers (examples include, but are not limited to, phosphate buffer, borate buffer, carbonate buffer, citrate buffer, HEPES, MEPS), salts (examples include, but are not limited to, the chloride, sulfate, and carbonate salts of sodium, zinc, calcium, ammonium and potassium), solubilizing agents (examples include, but are not limited to, urea, guanidine hydrochloride, guanidine sulfate and sarcosine), and stabilizing agents (examples include, but are not limited to, nonionic surfactants such as Tween 20, Tween 40, Tween 80, Brij, preservatives such as benzyl alcohol, and carbohydrates such as sucrose, raffinose, hydroxyethyl starch, dextran and trehalose).

A preferred container is a multiple-well (e.g., 96-well) sample holder, where multiple protein samples can be placed in an array of sample wells, with each well possibly containing solutions of different pH, ionic strength, salt type, buffer type, and stabilizing agents. Multiple-well sample holders may be conveniently sealed using commercially available self-adhesive plastic covers. The containers, or the entire multiple-well sample holder, may then be placed in a pressure vessel, such as those commercially available from the Flow International Corp. or High Pressure Equipment Co. The remainder of the interior volume of the high-pressure vessel may than be filled with water or other pressure transmitting fluid. The pressure may then be elevated as described in the claims, and dissolution and folding of the protein sample effected.

Disaggregation and refolding of proteins after viral inactivation processes. Viral inactivation processes are often used for human plasma, plasma-derived protein products and for cell culture media. These processes involve treatment of the solution with heat, high pressure cycling or solvent-detergent mixtures. For any of these methods, a problem arises in that the same process that inactivates viruses also causes protein denaturation and aggregation. Thus, a viral inactivation protocol often represents a compromise between optimal viral inactivation and optimal retention of desired levels of active protein. The result is that either the inactivation is incomplete, valuable protein components are lost, or both. The problem further is complicated by the fact that some of the most valuable proteins in the treated product (e.g., Factor VIII) are some of the most sensitive to stress-induced aggregation.

With the inventors' process, the solution containing viruses can be treated with any of the standard methods employed to inactivate viruses. After this treatment, the solution is then subjected to the inventors' high-pressure disaggregation and refolding processes to increase the level of native active protein(s). Furthermore, with the capacity to renature protein damaged during viral inactivation in place, more effective. (e.g., longer exposure to high temperatures and/or exposure to higher temperatures) viral inactivation processes could be employed.

Viruses that may be of concern include HIV-1, HIV-2, hepatitis A virus, hepatitis B virus, hepatitis C virus, parvovirus, herpes simplex virus I and II, Epstein Barr virus, HHV6 and cytomegalovirus. The sample may be plasma, blood, plasma-derived protein products, a protein product derived from cultured human cells, serum, or serum-containing cell culture medium. The high pressure protein refolding procedure further comprises one or more treatments including high temperature, chaotropic agent, solubilizing agent, reducing agent, agitation and "stepped" depressurization.

Reduction in levels of soluble aggregation that serves as nuclei or prenuclei for protein precipitation. There are several steps during the purification, storage and processing of protein products that foster formation of non-native soluble protein aggregates and/or insoluble precipitates on non-native protein aggregates. These include filtration, dialysis, chromatography, freeze-thawing, exposure to air bubbles during processes such as filling holding tanks or even final product vials, etc. Removing or reducing these aggregates would reduce the risk of loss of much greater amounts of protein during subsequent processing step due to precipitation. This is because soluble aggregates often serve as nuclei or prenuclei for precipitation. As such, these species can exist at relatively low levels (e.g., 1% of the total protein mass) and still trigger rapid precipitation of a large fraction (e.g., >30-50% or higher) of the total protein population. Precipitation can be triggered when a given processing step foster formation of a level of soluble aggregates that exceeds a threshold and/or by exposure of existing soluble aggregates to a stress (e.g., filtration) that promotes assembly to a critical nucleus size. Also, the mere fact of long-term storage can result in precipitation due to soluble aggregates.

Thus, in one embodiment, these nuclei or prenuclei can be removed simply by processing a whole cell slurry, or partially purified slurry, using the high pressure disaggregation and/or refolding processes of the present invention. Alternatively, precipitated protein can be separated from the soluble fraction by filtration, chromatography or centrifugation, and then refolded using the same high-pressure methods. The elimination (or even reduction in the level) of these aggregates minimizes the risk for protein precipitation in subsequent processing steps, and can improve shelf-life of refolding protein preparations.

The various aspects of the invention will be described in detail in the following discussion.

II. Definitions

As used herein, a "protein aggregate" is defined as being composed of a multiplicity of protein molecules wherein non-native noncovalent interactions and/or non-native covalent bonds such as intermolecular disulfide bonds hold the protein molecules together. Typically, but not always, an aggregate contains sufficient molecules so that it is insoluble. There are also abnormal oligomeric proteins which occur in aggregates in solution. In addition, there is typically (but not always) a display of at least one epitope or region on the aggregate surface which is not displayed on the surface of native, non-aggregated protein. "Inclusion bodies" are a type of aggregate of particular interest, to which the present invention is applicable.

"Atmospheric" or "ambient" pressure is defined as approximately 15 pounds per square inch (psi) or 1 bar.

A "binding partner," or "ligand," may be included in a refolding mixture. A "binding partner" is a compound which specifically binds (or otherwise interacts) with a target protein of interest. "Ligands" include, without limitation, antibodies, receptors, peptides, peptidomimetics, vitamins, cofactors, prosthetic groups, substrates, products, competitive inhibitors, metals and other small or large molecules. The presence of such a binding partner is especially advantageous in a refolding mixture where that binding partner favors a native conformation of the target protein when it interacts with the refolding target protein.

"Biological activity" of a protein as used herein, means at least 10% of maximal known specific activity as measured in an assay that is generally accepted in the art to be correlated with the known or intended utility of the protein. For proteins intended for therapeutic use, the assay of choice is one accepted by a regulatory agency to which data on safety and efficacy of the protein must be submitted. A protein having greater than 10% of maximal known specific activity is "biologically active" for the purposes of the invention.

"Denatured," as applied to a protein in the present context, means that native secondary and tertiary structure is disrupted to an extent that the protein does not have biological activity.

"Degassing" is defined as the removal of gases dissolved in solutions used in the present invention. Gas is much more soluble in liquids at high pressure as compared to atmospheric pressure and, consequently, any gas headspace in a sample will be driven into solution upon pressurization. The consequences are two-fold: the additional oxygen in solution may chemically degrade the protein product, and gas exiting solution upon depressurization may cause additional aggregation. Thus, samples should be prepared with degassed solutions and all headspace should be filled with liquid prior to pressurization.

"Depressurization" is a process of decreasing the pressure, from a high pressure, to a lower pressure (usually atmospheric or ambient presssure). Depressurization takes place over a predetermined period of time, ranging from 10 seconds to 10 hours, and may be interrupted at one or more points to permit optimal refolding at intermediate (but still increased compared to ambient) pressure levels. The depressurization or interruptions may be 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

"Heterologous" proteins are proteins which are normally not produced by a particular host cell. Recombinant DNA technology has permitted the expression of relatively large amounts of heterologous proteins (for example, growth hormone) from transformed host cells such as *E. coli*. These proteins are often sequestered in insoluble inclusion bodies in the cytoplasm and/or periplasm of the host cell. The inclusion bodies or cytoplasmic aggregates contain, at least in part, the heterologous protein to be recovered. These aggregates often appear as bright spots under a phase contrast microscope.

"High pressure," for the purposes of dissociating protein aggregates, means about 0.25 kbar to about 12 kbar. Specifically contemplated pressures within this range are 0.30 kbar, 0.35 kbar, 0.40 kbar, 0.50 kbar, 0.55 kbar, 0.60 kbar, 0.65 kbar, 0.70 kbar, 0.75 kbar, 0.80 kbar, 0.85 kbar, 0.90 kbar, 0.95 kbar, 1.0 kbar, 1.1 kbar, 1.2 kbar, 1.3 kbar, 1.4 kbar, 1.5 kbar, 1.6 kbar, 1.7 kbar, 1.8 kbar, 1.9 kbar, 2.0 kbar, 2.1 kbar, 2.2 kbar, 2.3 kbar, 2.4 kbar, 2.5 kbar, 2.6 kbar, 2.7 kbar, 2.8 kbar, 2.9 kbar, 3.0 kbar, 3.1 kbar, 3.2 kbar, 3.3 kbar, 3.4 kbar, 3.5 kbar, 3.6 kbar, 3.7 kbar, 3.8 kbar, 3.9 kbar, 4.0 kbar, 4.1 kbar, 4.2 kbar, 4.3 kbar, 4.4 kbar, 4.5 kbar, 4.6 kbar, 4.7 kbar, 4.8 kbar, 4.9 kbar, 5.0 kbar, 5.1 kbar, 5.2 kbar, 5.3 kbar, 5.4 kbar, 5.5 kbar, 5.6 kbar, 5.7 kbar, 5.8 kbar, 5.9 kbar, 6.0 kbar, 6.1 kbar, 6.2 kbar, 6.3 kbar, 6.4 kbar, 6.5 kbar, 6.6 kbar, 6.7 kbar, 6.8 kbar, 6.9 kbar, 7.0 kbar, 7.1 kbar, 7.2 kbar, 7.3 kbar, 7.4 kbar, 7.5 kbar, 7.6 kbar, 7.7 kbar, 7.8 kbar, 7.9 kbar, 8.0 kbar, 8.1 kbar, 8.2 kbar, 8.3 kbar, 8.4 kbar, 8.5 kbar, 8.6 kbar, 8.7 kbar, 8.8 kbar, 8.9 kbar, 9.0 kbar, 9.1 kbar, 9.2 kbar, 9.3 kbar, 9.4 kbar, 9.5 kbar, 9.6 kbar, 9.7 kbar, 9.8 kbar, 9.9 kbar, 10.0 kbar, 10.1 kbar, 10.2 kbar, 10.3 kbar, 10.4 kbar, 10.5 kbar, 10.6 kbar, 10.7 kbar, 10.8 kbar, 10.9 kbar, 11.0 kbar, 11.1 kbar, 11.2 kbar, 11.3 kbar, 11.4 kbar, 11.5 kbar, 11.6 kbar, 11.7 kbar, 11.8 kbar, 11.9 kbar, and 12.0 kbar. "High pressure" for the purpose of refolding steps, means about 0.25 to about 3.3 kbar. Specifically contemplated pressures within this range are 0.30 kbar, 0.35 kbar, 0.40 kbar, 0.50 kbar, 0.55 kbar, 0.60 kbar, 0.65 kbar, 0.70 kbar, 0.75 kbar, 0.80 kbar, 0.85 kbar, 0.90 kbar, 0.95 kbar, 1.0 kbar, 1.1 kbar, 1.2 kbar, 1.3 kbar, 1.4 kbar, 1.5 kbar, 1.6 kbar, 1.7 kbar, 1.8 kbar, 1.9 kbar, 2.0 kbar, 2.1 kbar, 2.2 kbar, 2.3 kbar, 2.4 kbar, 2.5 kbar, 2.6 kbar, 2.7 kbar, 2.8 kbar, 2.9 kbar, 3.0 kbar, 3.1 kbar, 3.2 kbar, 3.3 kbar.

A "host cell" is a microbial cell such as bacteria and yeast or other suitable cell including animal or a plant cell which has been transformed to express the heterologous protein of interest. Host cells which are contemplated by the present invention include those in which the heterologous protein expressed by the cell is sequestered in refractile bodies. An exemplary host cell is $E.\ coli$ K12, strain W311OG (pBGHI), which has been transformed to effect expression of the desired heterologous protein.

"Native conformation" of a protein, in the present context, refers to the secondary, tertiary and quaternary structures of a protein as it occurs in nature in its fully active state.

"Pressurization" is a process of increasing the pressure (usually from atmospheric or ambient presssure) to a higher pressure. Pressurization takes place over a predetermined period of time, ranging from 0.1 second to 10 hours. Such times include 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

"Proteins" include a wide variety of peptide-containing molecules, including monomeric, dimeric, multimeric, heterodimeric, heterotrimeric, and heterotetrameric proteins; disulfide bonded protein; glycosylated proteins; helical proteins; and α and β sheet-containing proteins. Particular proteins include hormones, antibodies, enzymes, and metal binding proteins.

"Refolding," "renaturing," or "naturing," in the present context, means the process by which a fully or partially denatured protein adopts secondary, tertiary and quaternary structure like that of the cognate native molecule. A properly refolded protein has biological activity that is substantially that of the non-denatured molecule. Where the native protein has disulfide bonds, oxidation to form native intramolecular disulfide bonds is a desired component of the refolding process.

A "surfactant" is a surface active compound which reduces the surface tension of water.

III. Reagents and Procedures

A. Chaotropic Agents

A chaotropic agent is a compound, including, without limitation, guanidine hydrochloride (guanidinium hydrochloride, GdmHCl), guanidine sulfate, urea, sodium thiocyanate, sarcosyl, sodium dodecyl sulfate, sodium octyl sulfate and/or other compounds which disrupt the noncovalent intermolecular bonding within the protein, permitting the polypeptide chain to assume a substantially random conformation.

Chaotropic agents, when employed, are used at "low" concentrations. Such low concentrations are 0 to about 4.5 M. Included are the particular concentrations of 0.1M, 0.2M, 0.3M, 0.4M, 0.5M, 0.75M, 1.0M, 1.25M, 1.5M, 1.75M, 2.0M, 2.25M, 2.5M, 3.0M, 3.5M, 4.0M, and 4.5M B. Reducing and Oxidizing Agents A reducing agent is capable of transferring electrons and, in so doing, "reducing" bonds between various atoms. In the context of the present invention, a reducing agent will disrupt intra- and intermolecular interactions, in particular, those involving disulfide bridges. Exemplary reducing agents, according to the present invention, are diothiothreitol, glutathione, dithioerythritol, or β-mercaptoethanol.

Oxidizing agents can be used to neutralize reducing agents. Oxidizing agents include oxidized glutathione, molecular oxygen, air, or peroxides C. Surfactants Surfactants are used to improve the solubility of certain proteins. Useful surfactants include nonionic (including, but not limited to, t-octylphenoxypolyethoxy-ethanol and polyoxyethylene sorbitan), anionic (e.g., sodium dodecyl sulfate) and cationic (e.g., cetylpyridinium chloride) and amphoteric agents. Suitable surfactants include, but are not limited to deoxycholate, sodium octyl sulfate, sodium tetradecyl sulfate, polyoxyethylene ethers, sodium cholate, octylthioglucopyranoside, n-octylglucopyranoside, alkyltrimethylammonium bromides, alkyltrimethyl ammonium chlorides, and sodium bis (2-ethylhexyl)sulfosuccinate.

D. Buffering Agents

Buffering agents are advantageously present in disaggregating and/or refolding mixtures to maintain a desired pH value or pH range. Inorganic buffer systems (phosphate, carbonate, among others) and organic buffer systems (citrate, Tris, MOPS, MES, HEPES, among others) are well known to the art.

E. Stabilizing Agents

Non-specific protein stabilizing agents act to favor the most compact conformation of a protein. Such agents include, but are not limited to, sucrose, trehalose, glycerol, betaine, amino acid(s), and trimethylamine oxide.

F. Spectroscopy

Another useful technique for optimizing refolding conditions is in situ spectroscopic measurement of samples under pressure. This is a well-known process for examining protein stability under pressure, but it has been underutilized in protein aggregation studies. Using high pressure spectroscopic techniques to observe aggregates dissolve under pressure will help determine the optimal pressure ranges for recovering proteins from aggregates. Custom made high pressure cells have been routinely used for high pressure unfolding studies and can be adapted for use in high pressure disaggregation and refolding.

IV. Current Methodologies for Protein Refolding

The following describe various generalized protein refolding technologies representing the "state of the art":

U.S. Pat. No. 5,077,392 (1991) describes a process for activation of recombinant protein produced in prokaryotes, in which the aggregated proteins are dissolved in 4-8M guanidine hydrochloride or 6-10M urea. Once solubilized, the buffer is dialyzed to a pH between 1 and 4. Finally, the solution is diluted to provide a nondenaturing and oxidizing environment to allow for refolding.

U.S. Pat. No. 5,593,865 (1997) describes a process for activating recombinant disulfide bond-containing eukaryotic proteins after expression in prokaryote hosts. Inclusion body proteins are dissolved in a strong denaturing agent (6M guanidine hydrochloride) containing reducing agents. In the refolding step, proteins are introduced into an environment which is oxidizing and nondenaturing.

U.S. Pat. 4,677,196 (1987) also describes purification and production of biologically active proteins from insoluble inclusion bodies. This is a general method for recovering proteins from insoluble form includes dissolving the protein aggregates in SDS. Once dissolved, the protein solution is separated from SDS by column chromatography. In the absence of SDS, the protein can refold. Finally, the protein is eluted from the column. Urea has also been included in dissolved protein solutions. After anion exchange chromatography, the urea from the refolded protein solution is removed by dialysis.

U.S. Pat. No. 5,605,691 (1997) describes solubilization of inclusion body proteins using SDS and heat. Once in solution, proteins are refolded by first diluting the SDS and then dialyzing away the SDS to nondenaturing concentrations.

U.S. Pat. No. 4,659,568 (1997) describes a process for solubilization, purification and characterization of protein from insoluble protein aggregates or complexes and compositions of matter therefrom. The insoluble protein aggregates or inclusion bodies are layered on top of a urea step gradient (3M to 7M urea). As the samples are centrifuged, the aggregates move through the gradient until they dissolve. This method provides a means of determining the urea concentration at which the protein dissolves.

U.S. Pat. No. 5,728,804 (1995) describes a process in which denatured or aggregated proteins are suspended in a detergent-free aqueous medium containing 5-7 M guanidine hydrochloride and incubated overnight. Once suspended, the sample is contacted with sufficient cyclodextrin to assist in the refolding of the proteins. Finally, the cyclodextrin is removed by dialysis.

The following are patents disclosing processes developed for refolding of particular proteins:

U.S. Pat. No. 4,652,630 (1987) describes a method for producing active somatotropin. In this method, the aggregates or inclusion bodies are solubilized in a chaotrope (3M to 5M urea), and the pH is adjusted to allow complete solubilization. Then the conditions are modified to allow oxidation in the presence of a nondenaturing concentration of chaotrope.

U.S. Pat. No. 5,064,943 (1991) also describes a method for solubilizing and renaturing somatotropin, but it does not require the use of a chaotrope. Here, the pH is adjusted to between 11.5 and 12.5 and maintained for 5 to 12 hours. Under these conditions, somatotropin will solubilize and renature.

U.S. Pat. No. 5,023,323 (1991) describes a process for naturation of somatotropin (growth hormone) aggregates in which the aggregates are dissolved in a denaturing chaotrope (1M to 8M urea). The solubilization step is followed by exposing the sample to an oxidizing environment in the presence of a nondenaturing concentration of chaotrope.

U.S. Pat. No. 5,109,117 (1992) describes a method in which somatotropin aggregates are dissolved in the presence of an organic alcohol and chaotrope (1M to 8M urea). Then the solubilized proteins are renatured in a nondenaturing, oxidizing environment.

U.S. Pat. No. 5,714,371 (1998) provides a method for refolding aggregates of hepatitis C virus protease. Aggregates are solubilized in 5M guanidine hydrochloride. Second, a reducing agent is added to the solution, and the pH is adjusted to provide an acidic pH. Third, the denaturing agent is removed from the solution by dialysis, and finally the pH is raised to its starting point.

U.S. Pat. No. 4,923,967 (1990) describes a process specific for human interleukin-2. Protein aggregates are dissolved in 4-8M guanidine hydrochloride with a sulfitolyzing agent. Once the proteins are dissolved, the sulfitolyzing agent is removed by solvent exchange. Finally, the temperature is raised to precipitate out interleukin-2 in pure form. To allow refolding, precipitates are dissolved again in guanidine hydrochloride plus a reducing agent. Finally, the solution is diluted to refold proteins.

U.S. Pat. No. 5,162,507 (1992) describes a process for recovering purified, oxidized, renatured recombinant interleukin-2 from microorganisms. Insoluble interleukin-2 isolated from microorganisms is solubilized in 2M to 4M guanidine hydrochloride. The guanidine hydrochloride solution is then diluted until the proteins precipitate out of the solution. The precipitates are then redissolved in a guanidine hydrochloride solution. The proteins are then oxidized to reform native disulfide bonds. Finally, the solution is diluted and interleukin-2 remains in solution.

U.S. Pat. No. 4,985,544 (1991) describes a process for renaturing fish growth hormone. In this process, the aggregates or inclusion bodies are dissolved using guanidine, urea, SDS, acid or alkali. The reducing agent is then removed, and an oxidizing agent is added. Finally, the denaturing agent is removed to allow refolding.

U.S. Pat. No. 5,410,026 (1995) describes a method in which insoluble, misfolded insulin-like growth factor-1 (IGF-1) is refolded into an active conformation. Once IGF-1 is isolated, it is incubated with 1-3M urea or 1M guanidine hydrochloride until the aggregates are solubilized and refolded.

Other U.S. patents dealing with protein refolding include U.S. Pat. Nos. 5,708,148; 4,929,700 and 4,766,224.

V. Agitation

Previous studies have demonstrated that agitation of proteins can result in aggregation and precipitation Bam et al. (1998). However, the general effects of mass transfer have largely been ignored in protein refolding. The present inventors have found, surprisingly, that physical mixing or "agitation" (stirring, shaking, rotation, etc.) increases both the speed and extent of protein refolding.

Thus, according to the present invention, agitation of proteins can be employed to assist or improve the refolding of proteins under pressure. Agitation can be applied to precipitated aggregates of proteins suspended in an aqueous medium under high pressure. Optimally, such agitation will be applied at intensities such that the precipitated protein aggregates are uniformly dispersed throughout the aqueous solution, but below levels where agitation-induced aggregation is favored. Such agitation should be applied as necessary to maintain the dispersion until such time as the protein disaggregates. Agitation can be accomplished using ultrasound or by pumping through static mixing devices.

VI. High Temperature Refolding

Although increased temperatures are often used to cause aggregation of proteins, the present inventors have determined that increased temperatures can enhance refolding recoveries effected by high pressure treatment, provided that the temperatures are not so high as to cause irreversible denaturation. Generally, the increased temperature for refolding should be about 20° C. lower than the temperatures at which irreversible loss of activity occurs. Relatively: high temperatures (for example, about 60° C. to about 125° C., about 80° C. to about 110° C., including about 100° C., about 105° C., about 110° C., about 115° C., about 120° C. and about 125° C.) may be used while the solution is under pressure, as long as the temperature is reduced to a suitably low temperature before depressurizing, Such a suitably low temperature is defined as one below which thermally-induced denaturation or aggregation occurs at atmospheric conditions.

VII. Dialysis and Dilution Under Pressure

Protein refolding under pressure appears to be independent of protein concentration. This is surprising given that high protein concentration is known to induce protein aggregation. However, while it is possible to obtain disaggregated, properly refolded protein at high concentrations, removal of the protein from pressure while still at high concentrations may result in re-aggregation. By the same token, running all pressurization steps under low concentration greatly increases the volume of material that must be processed, and hence increases the time factor. Alternatively, scaling up of the machinery to handle greater volumes will increase speed. However, the cost for scaling the pressurized aspects of the machinery is prohibitive.

Thus, the present inventors propose to conduct disaggregation and refolding experiments under high protein concentrations. "High" concentrations, depending on the protein in question, may range from 1 mg/ml to 100 mg/ml. Following disaggregation, and either during or after refolding, the protein is diluted to a storage stable concentration of 0.1 mg/ml to 10 mg/ml, preferably 1 mg/ml. This concentration is adjusted using various of the buffered solutions discussed above.

In addition, dialysis and dilution under pressure allow for changes in the chemical environment surrounding proteins while under pressure, for example, with reducing agents. Dialysis could be conducted in batch mode, where protein solutions are placed on one side of a dialysis membrane, and chemicals are allowed to diffuse across over time. However, proteins are too large to diffuse across the membranes utilized. In contrast, dilution would require an injection or mixing of two solutions while under pressure, creating a more sudden change in chemical conditions. In addition, one may wish to change pH of the solutions being used in the refolding process. For example, rates of disulfide exchange in the presence of redox agents are typically higher at pH 10-11, while secondary structural stability of proteins is typically higher at lower pH's. Thus, in addition to permitting removal of redox reagents, dialysis under pressure allows a concomitant change in pH.

VIII. "Stepped" Depressurization

In another aspect of the present invention, applicants provide "stepped" depressurization. This process comprises dropping the pressure from the highest pressure used to at least a secondary level that is intermediate between the highest level and ambient pressure. The goal is to provide an incubation period at or about this intermediate pressure zone that permits a protein to adopt a desired conformation.

In one embodiment, the present invention merely contemplates an intermediate pressure incubation that lies somewhere between the highest and ambient pressures. Alternatively, there are particular pressure ranges that may be suitable as "intermediate" pressure steps, including but not limited to about 50 MPa-500 MPa, about 100 MPa-400 MPa, and about 200 MPa-300 MPa. Particular levels for intermediate pressurization include about 100 MPa, about 150 MPa, about 200 MPa, about 250 MPa, about 300 MPa, about 350 MPa, about 400 MPa, about 450 MPa and about 500 MPa. The only limitation is that, when used, the foregoing pressures must be lower than the first or highest level of pressurization. Timing for intermediate depressurization steps include 1 min, 5 min, 10 min, 20 min, 30 min, 45 min, 1 h, 2 h 3 h, 4 h, 5 h, 6 h, 7 h, 8 h, 9 h, 10 h, 11 h and 12 h incubation periods.

IX. Batch versus Continuous Processing

Mechanically, there are two primary methods of high-pressure processing: batch and continuous. Batch processes simply involve filling a specified chamber, pressurizing the chamber for a period of time, and depressurizing the batch. In contrast, continuous processes constantly feed aggregates into a pressure chamber and soluble, refolded proteins move out of the pressure chamber. In both set ups, good temperature and pressure control is essential, as fluctuations in these parameters can cause inconsistencies in yields. Both temperature and pressure should be measured inside the pressure chamber and properly controlled.

Batch Samples: There are many methods for handling batch samples depending upon the specific stability issues of each protein. Protein solutions can be loaded directly into a pressure chamber, in which case refolding buffer would be used as the pressure medium. Alternately, samples can be loaded into any variety of sealed, flexible containers. This allows for greater flexibility in the pressure medium, as well as the surfaces to which the protein is exposed. Sample vessels could conceivably even act to protect the proteins of interest from chemical degradation (i.e., oxygen scavenging plastics are available).

Continuous Processing: With continuous processing, scale-up is simple. Small volumes under pressure can be used to refold large volumes of protein solutions. In addition, using an appropriate filter on the outlet of a continuous process will selectively release properly refolded proteins from the chamber while retaining both soluble and insoluble aggregates.

X. Multimeric Proteins

Many proteins that have potential uses in human disease therapies, prophylactic applications, and diagnostic applications are composed of multiple protein chains. Production of these proteins by recombinant techniques requires that the appropriate chains assemble to form the native secondary, tertiary, and quaternary structure. Improperly associated or unassociated chains are particularly prone to form non-native aggregates and precipitates. In one example, these non-native aggregates can be suspended in a suitable formulation in a sample container, placed in a commercially available high-pressure vessel such as those commercially available from the Flow International Corp. or High Pressure Equipment Co., and pressurized to disaggregate the protein and promote folding and assembly to the native structure. In another example, individual chains may be synthesized separately through well-known recombinant techniques. Purified or semi-purified solutions of individual chains may be combined in a sample holder in a suitable formulation, and placed in the aforementioned high-pressure vessel, and pressurized to effect folding and assembly to the native multimeric protein.

In particular embodiments, the invention provides for the refolding of multimeric proteins, such as dimers, trimers, tetramers, pentamers, hexamers, septamers, octamers, nonamer, etc. The polypeptide subunits can be identical (homodimer, etc.) or one or more can differ within the native protein (heterodimers, etc.). In a specific example discussed below, the protein is recombinantly produced human interferon-γ, which is a homodimer.

A. Interferon rhIFN-γ forms aggregates of completely different morphology when exposed to temperatures just below the onset of the thermal transition as compared to aggregates formed by exposure to mild concentrations of guanidine hydrochloride. Thermally-induced aggregates of rhIFN-γ are fibrous structure, whereas guanidine hydrochloride-induced aggregates form an amorphous precipitate. The secondary and tertiary structures of the aggregates, which are distinct from the native state, are independent of aggregate morphology.

Pressure is effective in the dissolution of both fibrous and amorphous aggregates of rhIFN-γ and in the recovery of the native structure, as measured by second derivative UV and FTIR. The rate of dissolution of the amorphous aggregates is rapid and acquisition of the pressure-dissociated state is achieved within 30 minutes at 250 MPa. The acquisition of the pressure-dissociated state from thermally-induced aggregates is approximately four times slower than that for the amorphous aggregates. However, once the pressure-dissociated state is achieved, the rate and extent of recovery of the native state (i.e., rate of refolding and yield), as measured by second derivative UV, is independent of the initial aggregate form.

The extent of refolding at 100 MPa for 1.5 hours was dependent on the protein concentration during refolding, with recovery of native-like structure increasing with decreasing protein concentration. For samples diluted to 1 mg/mL after the refolding protocol, the extent of refolding was independent of protein concentration during refolding. The differences in protein concentration dependence are attributed to a significant population of monomer remaining in the high protein concentration samples upon depressurization. Prompt dilution of the high protein concentration samples to 1 mg/mL following the refolding protocol results in conditions favoring refolding over aggregation, which proceeds via the monomer. As such, acquisition of dimer is essentially complete and is not affected by protein concentration during refolding. Failure to dilute the higher protein concentration samples after the pressure treatment results in conditions that favor aggregation over refolding and the high concentration of monomer leads to significant aggregation.

The equilibrium reaction of rhIFN-γ by pressure up to 250 MPa may be followed by second derivative UV spectroscopy. This equilibrium reaction is concentration dependent and is thus dissociation of the native dimer. The dissociation has a $\Delta V$ equal to $-209+/-13$ mL/mol of dimer, which is independent of protein and sucrose concentrations. Sucrose stabilizes rhIFN-γ against dissociation, via preferential exclusion at the protein surface, by shifting the equilibrium toward the more compact native state. The surface area change of dissociation was measured to be $12.7+/-1.6$ nm2/molecule of dimer, which represents a ca. 30% increase in the solvent-exposed surface area over the native dimer. A comprehensive equation was developed from experimental data that predicts the $\Delta G_{diss}$ of rhIFN-γ as a function of pressure, sucrose and protein concentrations.

Using similar criteria as the equilibrium dissociation, second derivative UV spectroscopy may be used to follow the rate of aggregation of rhIFN-γ. However, because similar criteria are used, solution conditions must be chosen so that significant dissociation does not occur coincident with aggregation. The inventors have shown that the $E_a$ for the first-order guanidine hydrochloride-induced aggregation was measured to be $130+/-30$ kJ/mol dimer, which is significantly different from the $E_a$ of the second-order thermally-induced aggregation process. The disparity in the activation energies for the aggregation reactions induced by the different stresses is confirmation that the kinetics of aggregation for the guanidine hydrochloride-induced aggregation are dominated by the N to 2M dissociation.

As was previously reported (Kendrick et al., 1998a), sucrose reduces the aggregation rate of rhIFN-γ in the presence of guanidine hydrochloride by preferential exclusion of sucrose from the protein surface, shifting the equilibrium toward the compact native state, N, and away from the expanded transition state, N*. However, pressure destabilizes rhIFN-γ to aggregation by guanidine hydrochloride through increased solvation of the protein. The increased solvation increases the exposed surface area of the protein, shifting the equilibrium away from N and toward N* and, in this way, counteracts the stabilizing effect of sucrose. The change in exposed surface area and change in partial molar volume between the expanded N* and N were found to be $3.5+/-0.2$ nm$^2$/molecule and $-39+/-9$ mL/mol of dimer, respectively. Thus, the perturbation required for the formation of the transition-state species, which leads to the formation of the aggregate competent monomer, is small in comparison to the difference between the native and dissociated states.

B. Other Multimers

Examples of other multimeric proteins which may be refolded according to the present invention include hemoglobin, lactic acid dehydrogenase, antibodies and antibody. fragments.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

High Pressure Disaggregation and Refolding

Procedure 1: High Pressure Protein Disaggregation and Refolding Varying Temperature Protein aggregation: Recombinant human growth hormone (rhGH) was suspended in 10 mM sodium citrate buffer (pH 6.0, 1 mM EDTA, 0.1% sodium azide) at a concentration of 1.5 mg/ml. 10 mL of rhGH solution was tumbled end over end in a 15 ml conical falcon tube at 8 rpm for at least 24 hours. Aggregates showing greater structural damage were tumbled under identical conditions with the addition of 0.75M guanidine hydrochloride in the citrate buffer.

Sample Preparation: One-half the required volume was centrifuged at 13,000 g for 15 minutes to sediment the insoluble aggregates. Supernatant was decanted and replaced with the final volume of buffer (10 mM sodium citrate buffer, pH 6.0, 1 mM EDTA, 0.1% sodium azide). The aggregate pellet was resuspended with an Ultrasonics brand sonicator (50% duty, 1 second pulse cycle). Once resuspended, samples were placed into 1 ml syringes (end heat-sealed and plunger in place to remove all headspace).

Pressurization and Analysis: After temperature had equilibrated, samples were placed into the pressure chamber. Pressure was increased to 2 kbar for 24 hours. Atmospheric samples were placed at an identical temperature. Pressure was released gently and evenly over 15 minutes. After depressurization, samples were centrifuged at 13,000 g for 15 minutes. Supernatant was analyzed for soluble protein by absorbance at 278 nm. Light scattering components were subtracted utilizing the method described by Leach & Scheraga (1960). The extinction coefficient for rhGH is 18,890 $(cm\ mol/l)^{-1}$.

Results of High pressure protein disaggregation and refolding varying temperature: In the absence of guanidinium, yields of refolded human growth hormone after pressure treatment increase with increasing temperature, reaching approximately 100% at a temperature of 60° C. Exposure to similar temperatures without high pressure treatment did not result in significant improvements in yields of folded, native proteins.

Procedure 2: Refolding Aggregates Using High Pressure Dialysis

Protein Aggregation and Sample Preparation: Hen egg white lysozyme (40 mg/ml) from Sigma Chemical Co. was denatured and reduced in 8M guanidine hydrochloride (GdmHCl), 40 mM DTT for one hour. The protein solution was then shock-diluted 20-fold with 50 mM Tris-HCl buffer (pH 8.0, 1 mM EDTA) to induce aggregation. Samples were then diluted an additional 2-fold with Tris-HCl buffer (pH 8.0+ GdmHCl+DTT) to create the final refolding solution to be placed inside the dialysis tubing (1 mg/mL lysozyme in 50 mM Tris-HCl pH 8.0, 0.8M GdmHCl, 100 mM DTT). Sample was then injected into dialysis tubing (3500 molecular weight cutoff, soaked overnight in Tris-HCl buffer, pH 8.0). Just prior to pressurization, the dialysis tubing was placed in a 25-fold volume excess of Tris-HCl buffer (pH 8.0, 0.8M GdmHCl, 3 mM oxidized glutathione) and sealed for pressurization.

Pressurization and Analysis: As quickly as possible following insertion of the dialysis tubing into the exchange buffer, samples were pressurized to 2 kbar. Pressure was maintained for 5 days. Samples were depressurized gently over 15 minutes. Once at atmospheric pressure, samples were centrifuged for 15 minutes at 13,000 g. to sediment insoluble aggregates. The supernatant was analyzed for enzymatic activity as previously described (St. John et al., 1999).

Example 2

High Pressure Refolding of Fibrous and Amporphous Aggregates of rhIFN-γ

Materials and Methods

Purified recombinant DNA derived rhIFN-γ in 5 mM sodium succinate, pH 5.0 (succinate buffer) was provided by Genentech Inc., stored at 4° C. until use and used without further purification. 40 mM pyridine acetate, pH 5.0 buffer (PyrAc buffer) was used for gas-phase electrophoretic mobility mass analysis (GEMMA). Succinate buffer was used in all other experiments. Protein standards (bovine serum albumin, glucose oxidase, hemoglobin, ubiquitin and thyroglobulin) were purchased from Sigma. All chemicals were of reagent grade or higher and were purchased from Sigma as well.

Aggregate preparation. Aggregates were prepared by inducing aggregation either by raising the solution temperature to 40° C. or by adding guanidine hydrochloride to the protein solution such that the final guanidine hydrochloride concentration was 0.45 M. The extents of the aggregation reactions were in excess of 95% in all cases. The inventors have determined the extent of reactions from the well-characterized aggregation rates both for the thermally-induced aggregation, and found second-order in protein concentration; for the guanidine hydrochloride-induced aggregation reaction, first-order in protein concentration. Guanidine hydrochloride-induced aggregates were washed with sufficient fresh buffer so that the final guanidine hydrochloride solution concentration was below 5 mM. Aggregates for refolding experiments were suspended in fresh buffer at approximate concentrations of 1, 10 and 20 mg/mL rhIFN-γ.

High-pressure experiments. The high-pressure equipment used for refolding experiments consisted of a high-pressure reactor, high-pressure UV spectroscopy cell, metallic gauge (accurate to +/−2 MPa) and generator. The high-pressure reactor and high-pressure UV spectroscopy cell were designed and fabricated in the inventors' laboratory. The gauge and generator were purchased from High Pressure Equipment, Co, (Erie, Pa.). For any given experiment, either the high-pressure reactor or high-pressure UV spectroscopy cell was employed.

The high-pressure UV spectroscopy cell was made of 316 stainless steel, sealed with Buna-N 90 durometer o-rings and had an optical port diameter of 6 mm and pathlength of 7.65 mm. The cell utilized cylindrical sapphire windows (16 mm diameter, 5.1 mm thick) and was capable of experiments up to 250 MPa. Separation of the sample from the pressure transmitting fluid (silicon oil) was facilitated by a piston device external to the cell. All wetted metal surfaces were constructed of 316 SS. All in situ high-pressure UV experiments were conducted at a protein concentration of ca. 1 mg/mL.

For experiments conducted in the high-pressure reactor, aggregate suspensions were loaded into ca. 1 mL polypropylene bulbs, heat-sealed and loaded into the reactor. The reactor was sealed and the pressure increased to 250 MPa, which is sufficient pressure to ensure that, at equilibrium, rhIFN-γ is fully dissociated into monomers, as determined by the inventors. The samples were held at 250 MPa for sufficient time to dissolve the aggregates and for the protein equilibrate, based upon in situ second-derivative UV measurements (see below). The pressure was then lowered to 100 MPa and again held for sufficient time to reach equilibrium for rhIFN-γ concentrations of ca. 1 mg/mL (see below), after which the pressure was reduced to 0.1 MPa and the samples were removed from the high-pressure reactor.

Transmission Electron Microscopy (TEM). TEM was performed on samples of native, aggregated and pressure-treated aggregates rhIFN-γ that had been negatively stained with a 2% solution of uranyl acetate at total a protein concentration of ca. 1 mg/mL. Specimens were stained on formvar/carbon 400 mesh copper grid and were viewed on a JOEL 100CX TEM with an accelerating voltage of 80,000 kV. Micrographs of aggregate structures were obtained at magnifications from 20,000 to 80,000.

Gas-phase electrophoretic mobility mass analysis (GEMMA). The procedure for GEMMA particle size analysis was based on the method of Kaufman et al. (1996) (Kaufman et al., 1996). The instrument was calibrated using protein standards of known molecular weight (MW). A linear calibration curve was developed from the natural log of the electrophoretic mobility (EM) diameters versus the natural log of MW. Samples of native, aggregated and pressure-treated aggregates of rhIFN-γ were diluted to ca. 1 to 2 μg/mL into PyrAc buffer, which has a conductivity of ca. 2 mΩ$^{-1}$ cm, and immediately analyzed using a GEMMA analyzer from TSI (St. Paul, Minn.). PyrAc buffer was employed due to the GEMMA requirement of less than 1 ppm non-volatile material in the sample.

The GEMMA analyzer consisted of a model 3480 electrospray aerosol generator, a model 3085 differential mobility analyzer (DMA), a model 3025A ultrafine condensation particle counter (CPC). Dried and filtered air was delivered at a rate of 1 Lpm from the utility air supply through a model 307402 filter/dryer and instrument-grade carbon dioxide was delivered at a rate of 0.05 to 0.1 Lpm. The fused-silica electrospray capillary was 25 cm long and had an internal diameter of 25 μm. Sample flow (ca. 100 nL/min) was facilitated by a differential pressure of 25 kPa (3.7 psi) across the capillary. An electrical potential of 2 kV was maintained across the capillary, with a corresponding current of 200 to 250 nA.

Data acquisition was made via Aerosol Instrument Manager (AIM©) version β4.10 software from TSI on an IBM compatible PC running Microsoft Windows 95©. The data acquisition software used 64 log-spaced channels per decade of EM diameter. Sample analysis was made from ca. 2.5 to 58 nm and acquisition times from 3 to 6 minutes, using assumed values for air viscosity ($\mu$) of $1.82 \times 10^{-5}$ kg/(m s), mean free path ($\lambda$) of $7.75 \times 10^{-8}$ m and protein density ($\rho$) of 1.2 g/mL. Data files, in units of mass percent concentration, were exported as text files and imported into Microsoft Excel©. EM diameters were determined by the maximum of a given peak. Monomer to dimer ratios and extent of reactions (based on mass percent dimer) were determined by finite integration of the individual peaks in the mass percent distributions.

Dynamic light scattering (DLS). Dynamic light scattering measurements were performed on the thermally-induced aggregates of rhIFN-γ using a Nicomp 370 Submicron Particle Sizer (Particle Sizing Systems, Santa Barbara, Calif.). The total protein concentration was 1 mg/mL.

Derivative UV spectroscopy. Absorption spectra were measured with a Perkin-Elmer Lambda 3B dual-beam spectrophotometer at rhIFN-γ concentrations of ca. 1 mg/mL. Scans were measured from 310 nm to 250 nm with scan rate of 15 nm per minute. Data acquisition was made via a National Instruments (Austin, Tex.) model AT-MIO-16E-10 data acquisition board at a rate of 5 samples per second. National Instruments LabView© software was used to control data acquisition and Microsoft Excel© to convert the wavelength and absorption data from volts to nm and absorbance units, respectively. The second derivatives of the absorption spectra ($d^2A/d\lambda^2$) were calculated in Grams/386 (v. 3.02) software (Galactic Industries) using the Savitzky-Golay method with a second order polynomial smoothed over +/−2 nm.

Temperature was controlled using recirculating fluid thermostated by a Lauda model M3 recirculating bath temperature controller. Spectra for samples treated in the high-pressure reactor were collected at atmospheric pressure with the samples in standard 10 mm pathlength quartz cuvettes and the appropriate blank placed in the reference cell of the spectrophotometer. For experiments carried out in the high-pressure cell, absorption spectra were collected for the sample and buffer separately, with no reference sample in the spectrophotometer. Subtraction of the buffer spectrum, collected at the appropriate pressure, from the protein spectrum was carried out in Grams/386 (v. 3.02) software prior to calculation of the second derivative.

Fourier Transform IR Spectroscopy (FTIR). IR spectra were collected using an adjustable pathlength cell set at 8 μm. Blank buffer spectra were collected using the same cell under an identical solution condition, with no protein present. All spectra were collected at atmospheric pressure on a Nicolet Magna-IR© 750 series II (Madison, Wis.) spectrometer equipped with a DTGS detector. Interferograms were collected in the single beam mode, signal-averaged over 256 (for samples at ca. 20 mg/mL) and 1024 (for samples at ca. 10 mg/mL) scans at a resolution of 4 cm$^{-1}$ using Omnic© (v. 2.1) Software from Nicolet. The optical bench and sample chamber were continuously purged with dry air supplied from a Whatman model 75-52 FTIR purge gas generator (Haverhill, Mass.). Single beam spectra of both protein-in-buffer and buffer were reprocessed into absorbance spectra by subtracting out the background spectra from each. Nicolet software was used to subtract the buffer and water vapor contributions from the protein-in-buffer spectra and to calculate the second derivative. The remaining spectrum was 7-point smoothed to remove white noise and imported into Grams/386© (v. 3.02) software (Galactic Industries) where it was baseline corrected and area normalized per method of Dong et al., 1995.

Size Exclusion Chromatography (SEC). The presence of soluble aggregates and monomer/dimer content of pressure-treated aggregates was measured by SEC and compared to the liquid control. Insoluble aggregates were removed by centrifugation and the supernatant was assayed by size exclusion chromatography (SEC). 50 μL aliquots of the supernatant, diluted to 1 mg/mL in succinate buffer, were loaded onto a silica-based Tosohaas TSK-GEL G2000SW$_{XL}$ column. The mobile phase, 1.2 M KCl, was pumped at a rate of 0.8 mL/min and absorbance at 214 nm was monitored as a function of time. Resultant chromatograms were imported into Grams/386© (v. 3.02) software where they were area normalized and curve fit to determine the percent contributions and elution times for the monomer and dimer. The Autofind curve fit function was employed with parameters set for a maximum of two peaks, Guassian curve, medium sensitivity and offset baseline. The instrument was calibrated using protein standards of known MW. A linear calibration curve was developed from the natural log of the elution time versus the natural log of MW.

Results and Discussion

Characterization of aggregates: Physical characterization. At protein concentrations above 5 mg/mL, thermally-induced aggregates of rhIFN-γ formed a colorless, transparent gel with high viscosity that could not be concentrated by centrifugation. At concentrations of ca. 1 mg/mL, the protein concentration was sufficiently low that the viscosity increase upon aggregation was minimal and separation by centrifugation was possible. Like the aggregates formed at higher protein concentrations, the aggregates formed at concentrations of ca. 1 mg/mL were colorless and scattered relatively little light. In contrast to aggregates formed by high temperatures, the addition of guanidine hydrochloride to solutions of rhIFN-γ resulted in the formation of a white, opaque precipitate that was easily centrifuged from solution, regardless of the aggregation protein concentration.

Figures 1, 2A:
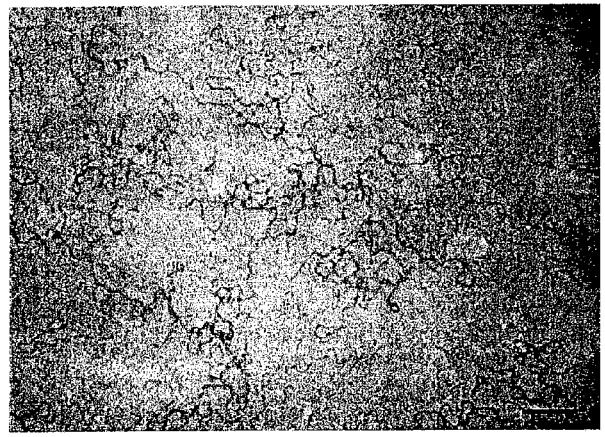
FIGS. 2A-2B: TEM micrographs of rhIFN-γ (FIG. 2A) thermally-induced aggregates and (FIG. 2B) guanidine hydrochloride-induced aggregates. Frames A1 and B are at a magnification of 40,000 (Bar=200 μm) and A2 at 80,000 (Bar=100 μm).
Figures 2, 2A:
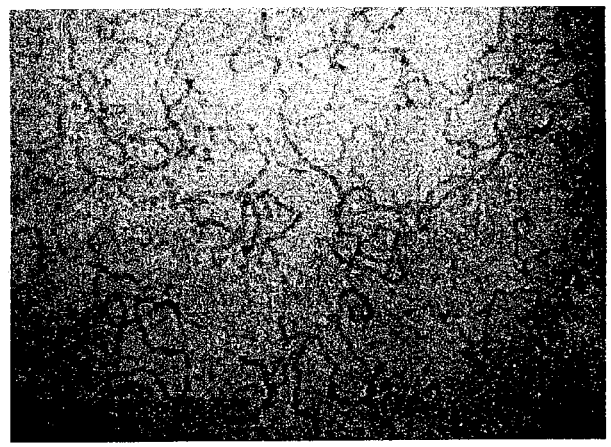
Figure 2B:
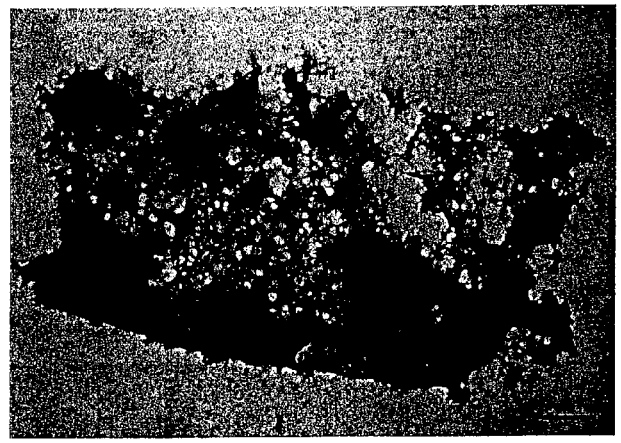

Electron micrographs of the aggregates revealed that the thermally-induced aggregates formed a matrix of fiber-like strands of indeterminate length (FIG. 2A), but the guanidine hydrochloride-induced aggregates formed an amorphous precipitate (FIG. 2B). The thermally-induced aggregate fibrils have a consistent diameter on the order of 10 nm. No amorphous structures were observed in the thermally-induced aggregates. Conversely, no fibrous structures were found in the guanidine hydrochloride-induced aggregate samples.

Figure 3A:
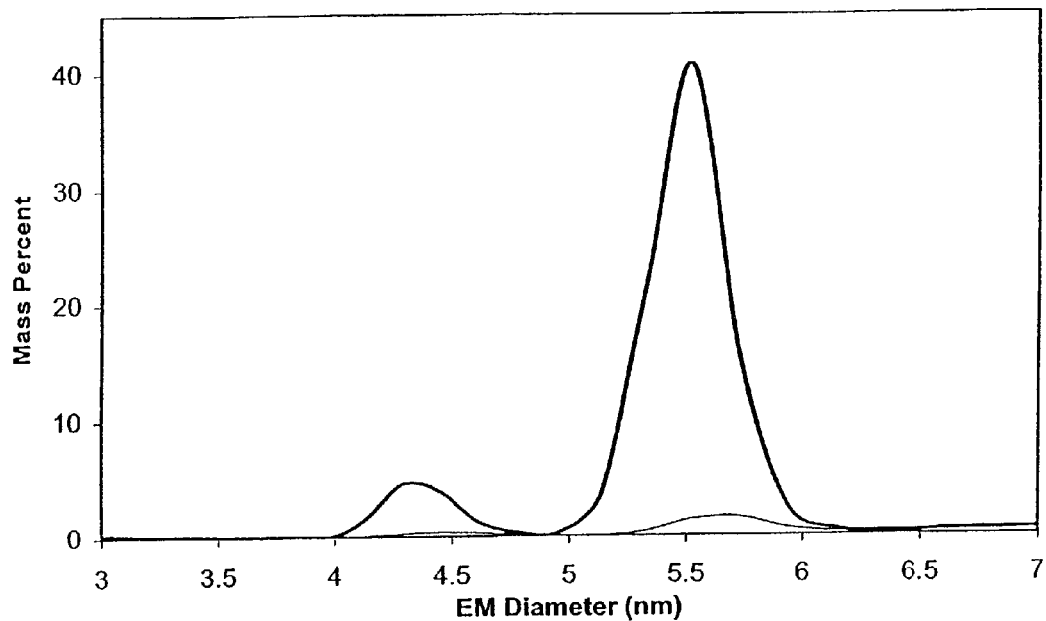
FIG. 3: Mass percent concentration versus EM diameter as measured by GEMMA for native (thick line) and thermally-induced aggregates (thin line) of rhIFN-γ. (A) EM diameter region for monomer (ca. 4.4 nm) and dimer (ca. 5.5 nm) and (B) EM diameter region for aggregates. Note that the particle size distribution is split into two windows for clarity and that the two windows have different mass percent scales. The response for native rhIFN-γ in the 7 to 10 nm range (window B) is within the noise level of the instrument.
Figures 1, 7A:
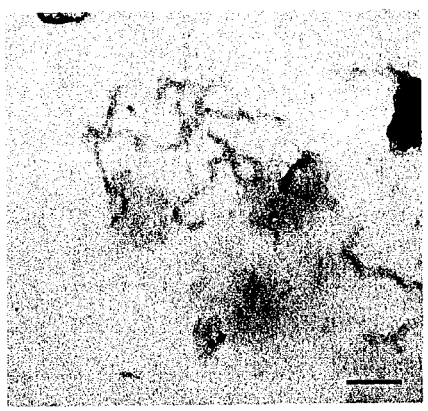
FIGS. 7A-7C: TEM micrographs of pressure-treated (FIG. 7A) thermally-induced aggregates, (FIG. 7B) guanidine hydrochloride-induced aggregates and (FIG. 7C) native control rhIFN-γ (no pressure treatment) at magnifications of 40,000. Short fibrous structures were observed in all samples, but the dominant structure was amorphous (e.g., A2). Bar=200 μm.
Figure 7B:
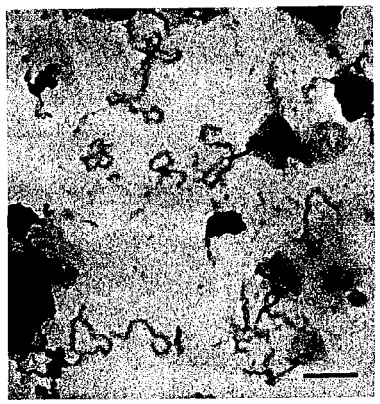
Figures 2, 7A:
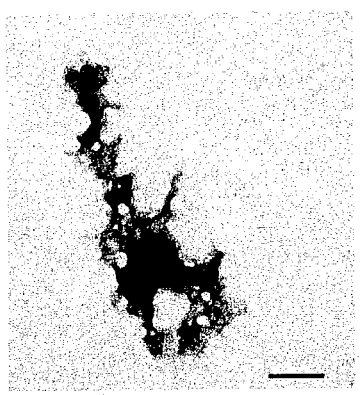
Figures 1, 7C:
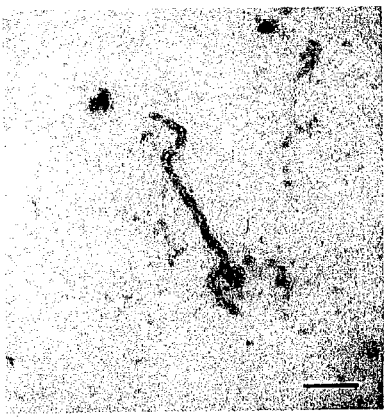
Figures 3, 7A:
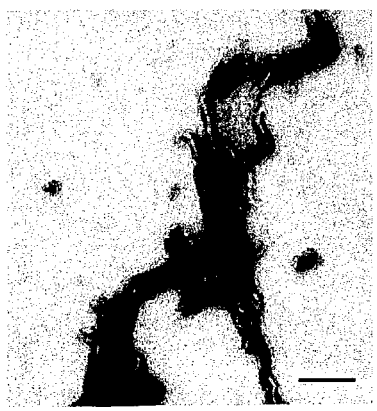
Figures 2, 7C:

The EM diameter distribution of native rhIFN-γ and thermally-induced aggregates was measured by GEMMA and the results are presented in FIG. 3. The native protein, equilibrated at 25° C. and 1 mg/mL in PyrAc buffer, was found to have two significant peaks centered at 4.4 and 5.5 nm (FIG. 3A). The peaks corresponded to particles having molecular weights of 16 and 32 kD, respectively, based on the calibration curve with known protein standards. These molecular weights are in good agreement with the known molecular weights for the monomer and dimer of rhIFN-γ (16.45 and 32.9 kD, respectively). No other significant peaks were detected in the native sample if the concentration of the sample was kept below ca. 3 μg/mL. The mass percent monomer detected by GEMMA (ca. 12% in FIG. 3A) has been determined to be artificially high from dissociation equilibrium experiments. The bias towards the monomer is caused by surface-induced dissociation of the native dimer on the electrophoresis capillary. Corrected mass percent monomer for native rhIFN-γ, and EM diameters and effective molecular weights for the monomer and dimer, as determined by GEMMA, are reported in Table 1A.

TABLE 1A

Comparison of GEMMA results between the native control and pressure-treated aggregates of rhIFN-γ.

|  | Native control | Pressure-treated aggregate |
| --- | --- | --- |
| Mass percent monomer | 1.4 +/− 3.5%[1] | 12 +/− 3.5%[1] |
| Monomer EM diameter | 4.4 nm | 4.6 nm |
| Dimer EM diameter | 5.5 nm | 5.7 nm |
| Monomer effective MW[3] | 16 kD | 18 kD |
| Dimer effective MW[3] | 32 kD | 36 kD |

TABLE 1B

Comparison of SEC results between the native control and pressure-treated aggregates of rhIFN-γ.

|  | Native control | Pressure-treated aggregate |
| --- | --- | --- |
| Mass percent monomer[2] | 6.4 +/− 1.5% | 4.2 +/− 1.5% |
| Monomer elution time | 889 +/− 1 s | 889 +/− 1 s |
| Dimer elution time | 830 +/− 1 s | 821 +/− 1 s |
| Monomer effective MW[4] | 16 kD | 16 kD |
| Dimer effective MW[4] | 33 kD | 35 kD |

*There was no observed effect with aggregate type or refolding concentration.
[1]Corrected mass percent monomer calculated from the measured equilibrium constant.
[2]Calculated by Guassian curve-fit using Grams/386 © (v. 3.02) as described in text.
[3]Calibration curve presented elsewhere.
[4]Calibration curve not shown.

Figure 3B:
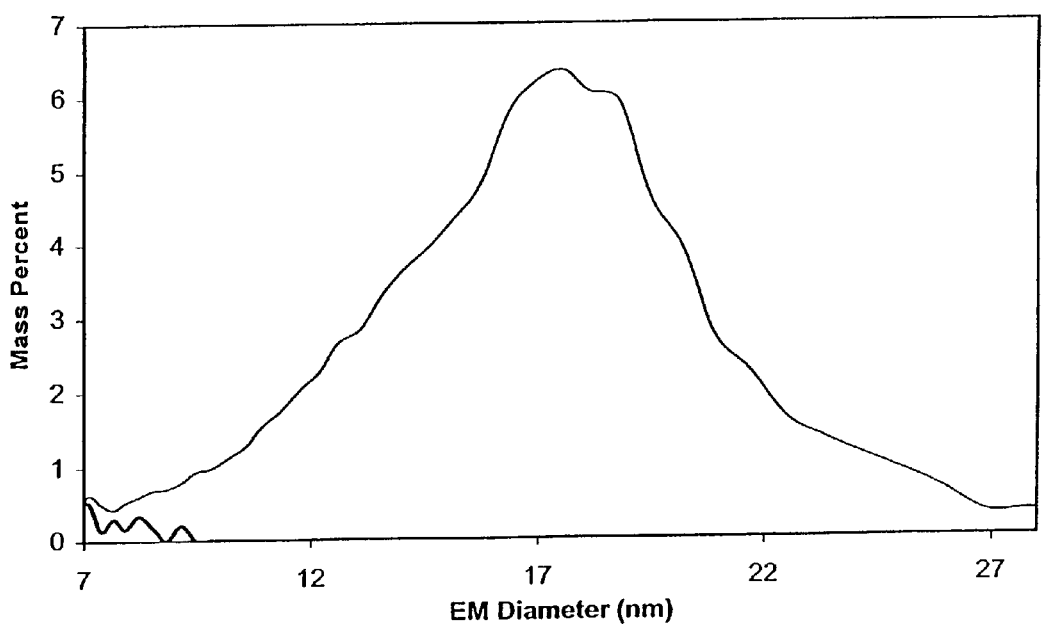

The thermally-induced aggregate sample, aggregated at 40° C. and 21 mg/mL for 48 hours in succinate buffer, had ca. 1 and 4% by mass of monomer and dimer, respectively. The aggregates (FIG. 3B), in excess of 95% by mass, had a mass average diameter of 16.5 nm, corresponding to an average effective MW of 980 kD based on the calibration curve with known protein standards. The effective diameter from GEMMA agreed poorly with DLS results, which indicated an effective hydrodynamic diameter of 1900 nm, and the fact that the aggregates were visible to the eye. It is likely that, as droplets are formed at the exit of the capillary, the fibrous aggregates are sheared into smaller aggregates (Kaufman, 2000). Thus, it was determined that GEMMA is not an appropriate technique for assessing the size of the aggregates, but is appropriate for detecting the presence of aggregates and determining the mass percent aggregate. The particle diameter obtained from DLS measurements was considered inaccurate due to the morphology of the thermally-induced aggregates and was used only for gross comparison with the GEMMA result. Guanidine hydrochloride-induced aggregates were not analyzed by GEMMA due to the requirement of less than 1 ppm non-volatile material in the sample.

Characterization of aggregates: Structural characterization. The region between 275 and 295 nm of the second derivative UV spectrum reflects the microenvironments of tryptophan and tyrosine residues and is affected by the conformational state of proteins (Balestrieri et al., 1978; Ragone et al., 1984; Servillo et al., 1982). Since the derivative UV spectra of tyrosine and tryptophan are minimally affected by pressure (Lange et al., 1996), changes to the second derivative UV spectrum of rhIFN-γ by pressure result from changes to the native conformation, as shown by the inventors here. The second derivative UV spectra of native, pressure dissociated soluble protein and thermally-induced and guanidine hydrochloride-induced aggregate forms of rhIFN-γ in 5 mM sodium succinate buffer are presented in FIG. 4. The wavelength position of the extremum located near 286 nm for native and dissociated forms of rhIFN-γ is independent of the degree of dissociation and its relative height has been shown by the inventors to indicate the degree of dissociation of rhIFN-γ. Thus, the relative height of this extremum can also be used to follow the extent of reassociation and refolding of rhIFN-γ in the absence of aggregates.

Figure 4:
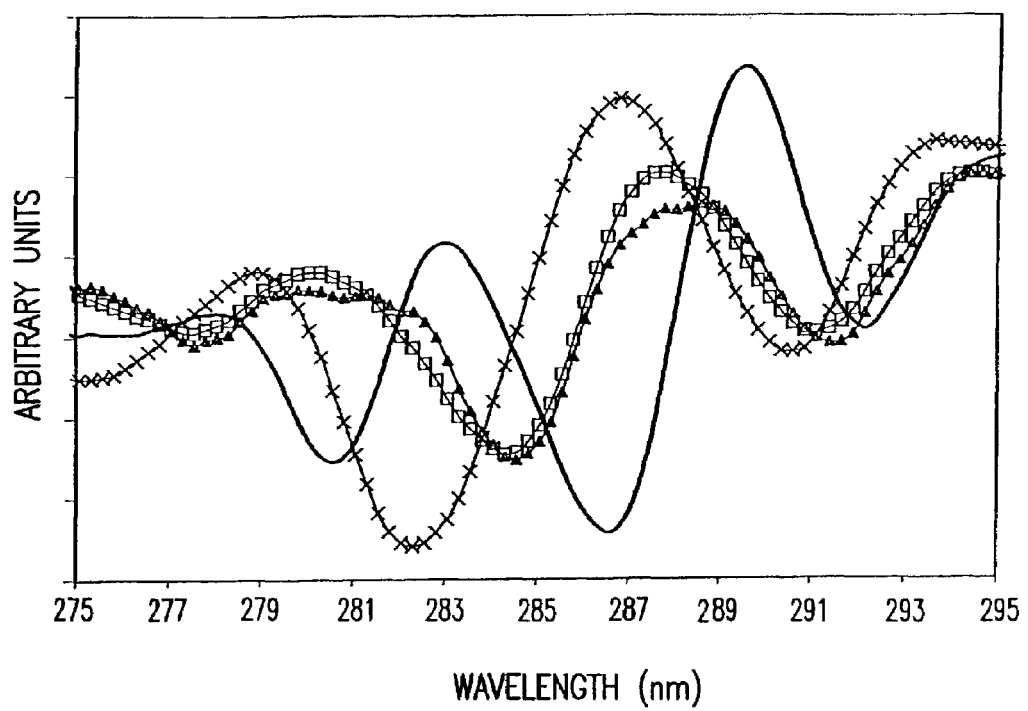
FIG. 4: Second derivative UV spectra of rhIFN-γ thermally-induced (□) and guanidine hydrochloride-induced (▲) aggregates prior to pressure treatment. Included with the spectra of aggregates are rhIFN-γ liquid control at 0.1 MPa (solid line) and pressure-dissociated at 250 (X) MPa. The extremum near 286 nm in the native and pressure-dissociated spectra was used to follow the refolding event after dissociation of aggregates. Except for the 250 MPa spectrum, all spectra were collected at 0.1 MPa.

The spectra of the two aggregate forms (thermal- and guanidine hydrochloride-induced) show similar deviations from the native second derivative UV spectrum and are distinct from the both the native and pressure-dissociated spectra (FIG. 4). The aggregate spectra display an overall dampening of the signal amplitude and a blue-shift in the absorbance spectra, both of which indicate increased exposure to hydrophilic environments of the tryptophan and tyrosine residues relative to the native structure (Lange et al., 1996; Mach & Middaugh, 1994). Additionally, both aggregate spectra show significant reduction in the depth of the minimum located near 280 nm. However, there are notable differences between the aggregate second derivative UV spectra. The extent of perturbation from the native spectrum, as measured by amplitude reduction and wavelength shift, is less severe with the thermally-induced aggregate spectrum compared with the guanidine hydrochloride-induced aggregate spectrum. Further, there is significant band broadening in the maxima located near 288 and 280 nm for the guanidine hydrochloride-induced aggregate spectrum that is not apparent in the thermally-induced aggregate spectrum.

Figure 5:
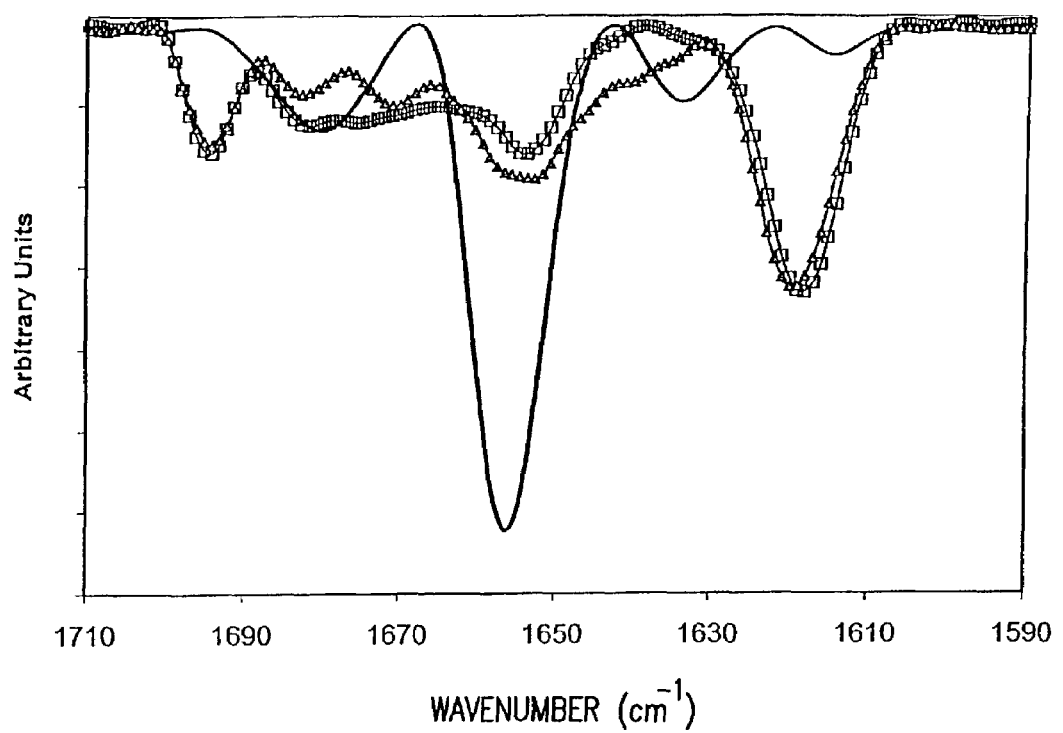
FIG. 5: Area normalized second derivative FTIR spectra of thermally-induced aggregates (□) and guanidine hydrochloride-induced aggregates (▲) prior to pressure treatment. The spectrum of native rhIFN-γ is included for comparative purposes and is represented as a solid line. All spectra were collected at 0.1 MPa.

To compare the secondary structures of the two aggregates with each other as well as the native form, FTIR absorbance spectra of all three states were collected and second derivative spectra calculated and compared. FIG. 5 is a plot of the second derivative FTIR spectra of native rhIFN-γ in buffer and both the thermal- and guanidine hydrochloride-induced aggregates of rhIFN-γ. Significant perturbations from the native state are observed in both aggregate forms, with a wavelength shift and a loss of absorbance in the α-helix band (near 1656 $cm^{-1}$ in the native spectrum) and concomitant appearance of intermolecular β-sheet bands near 1620 and 1695 $cm^{-1}$ (FIG. 5). The contributions of the intermolecular β-sheet bands near 1620 and 1695 cm$^{-1}$ are comparable for both aggregate forms, as is the extent of loss in α-helix. Only minor differences in β-sheet (region near 1630 to 1645 cm$^{-1}$) and turn structures (region near 1670 to 1685 cm$^{-1}$) are apparent between the temperature- and guanidine hydrochloride-induced aggregates.

Figure 6A:
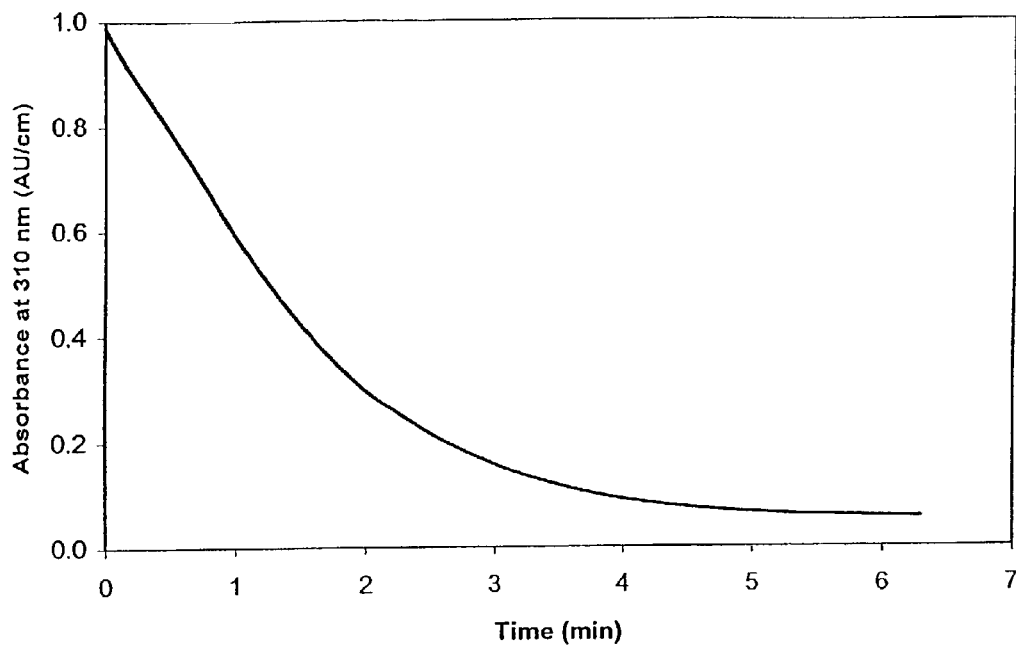
FIGS. 6A-6B.

High pressure dissolution and refolding kinetics. Pressure is known to disfavor the higher-order association of protein subunits (Silva & Weber 1993) and therefore may be employed to dissociate aggregates, as has been previously demonstrated (Foguel et al., 1999; Gorovits & Horowitz 1998; Silva et al., 1989; St. John et al., 1999). When guanidine hydrochloride-induced aggregates of rhIFN-γ were exposed to 250 MPa, there was rapid and complete loss of light-scattering aggregates, as measured by absorbance at 310 nm (FIG. 6A). The total rhIFN-γ concentration was 1 mg/mL and the guanidine hydrochloride concentration in solution was ca. 5 mM. Once dissolution of the aggregates was complete, absorbance scans were collected at 250 MPa and derivative spectra calculated. The pressure was maintained at 250 MPa until the second derivative spectrum no longer changed with time (ca. 30 minutes). The inventors found that second derivative spectrum of guanidine hydrochloride-induced aggregates at 250 MPa equilibrated to the spectrum obtained when native rhIFN-γ is dissociated with pressure at 250 MPa (FIG. 4), indicating complete disruption of the aggregate structure and dissociation of the dimeric structure to monomer.

Figure 6B:
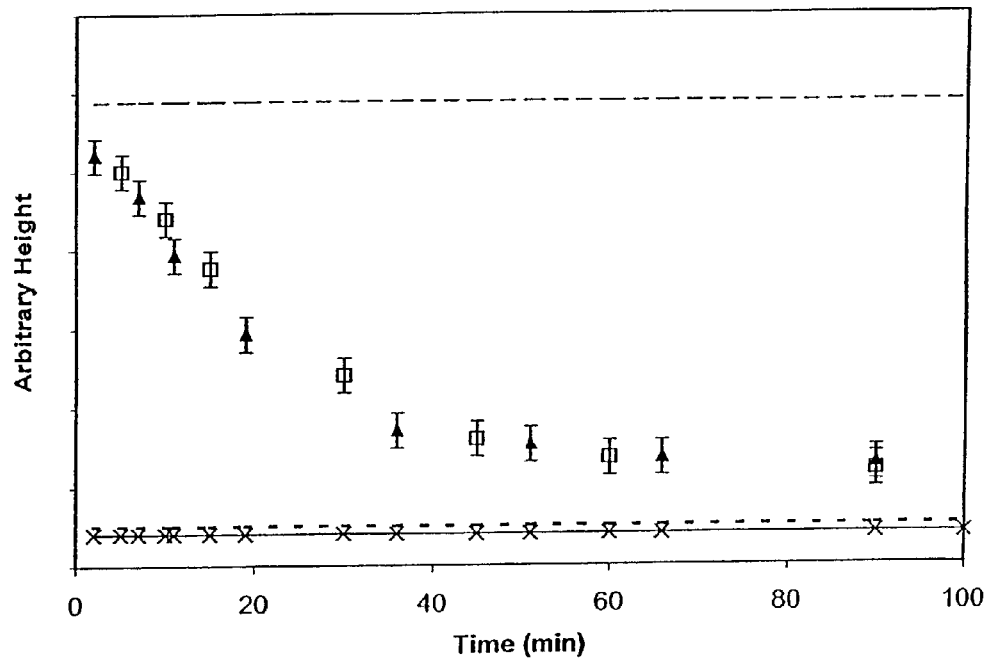

Once the second derivative spectrum displayed no further changes with time at 250 MPa, the pressure was reduced to 100 MPa and absorbance spectra collected over time. The second derivative spectra were again calculated and compared until changes with time were no longer observed. At 100 MPa, the extremum near 286 nm (a maximum in the pressure dissociated spectrum, see FIG. 4) decreased in height with time and eventually became a minimum as the protein began to assume a more native conformation. FIG. 6B is a plot of the height of the extremum near 286 nm versus time at 100 MPa for the reassociation/refolding of rhIFN-γ at 1 mg/mL, after the guanidine hydrochloride-induced aggregates were dissociated at 250 MPa. Superimposed on FIG. 6B are heights of the spectra for the pressure dissociated and native forms of rhIFN-γ as well for the equilibrium pressure-refolded form (1 mg/mL rhIFN-γ), achieved by lowering the pressure to 0.1 MPa. The refolding at 100 MPa is complete in ca. one hour and the 286 nm extremum height of the pressure-treated aggregate has returned nearly completely to that of the native control.

The rate of dissolution of thermally-induced aggregates at pressure could not be quantified by absorbance changes at 310 nm with time because the aggregates did not scatter light sufficiently. As well, the dissolution of aggregates at pressure can not be followed in the region between 275 and 295 nm either because aggregate dissolution and structural migration to the pressure-dissociated form (FIG. 4) occur simultaneously. Thus, the rate of thermally-induced aggregate dissolution at pressure cannot be directly compared with the pressure dissolution of guanidine hydrochloride-induced aggregates. However, the time required for the thermally-induced aggregate to assume the pressure-dissociated state (ca. 2 hours), measured by second derivative UV, is significantly slower compared to the time required for guanidine hydrochloride-induced aggregates (ca. 30 minutes) to assume the pressure-dissociated state (data not shown). But once the pressure-dissociated state is achieved, the refolding rates are comparable (FIG. 6B).

Characterization of pressure-treated aggregates. Thermally- and guanidine hydrochloride-induced aggregates of rhIFN-γ in buffer at protein concentrations of ca. 1, 10 and 20 mg/mL were pressurized to 250 MPa for five hours. The pressure was then lowered to 100 MPa for one and one-half hours, then again lowered to 0.1 MPa. Analysis of the pressure treated aggregates was made both immediately following and two weeks after pressure treatment to assess the effectiveness of the pressure treatment on acquisition of native-like characteristics from aggregates and the stability of the pressure-treated aggregates against re-aggregation, respectively. TEM, GEMMA and HPLC were employed to physically characterize the pressure-treated aggregates and second derivative UV and FTIR spectroscopies were used to structurally characterize the pressure-treated aggregates. Comparison of the results for each technique was made among the pressure-treated aggregates, the aggregate controls and native liquid rhIFN-γ control.

Physical characterization after pressure treatment. Upon depressurization, all thermally- and guanidine hydrochloride-induced aggregate samples were optically clear with no particulates visible to the eye. Additionally, the 10 and 20 mg/mL thermally-induced aggregate samples, which were gelatinous solids prior to pressure treatment, were liquids with viscosities indistinguishable (judged qualitatively) from the native liquid controls.

TEM was performed on the liquid control and on the 1 and 20 mg/mL (pressurized and control) samples for both types of aggregates at a total protein concentration of ca. 1 mg/mL (20 mg/mL samples were diluted immediately after pressure treatment). FIG. 7 contains representative TEM micrographs of pressure-treated (A) thermally-induced and (B) guanidine hydrochloride-induced aggregates of rhIFN-γ along with (C) the liquid control. Aggregate controls were unchanged from the structures initially observed and, therefore, micrographs of the aggregate controls are not presented in FIG. 7 (see FIG. 2 for representative structures of the aggregate controls). All micrographs in FIG. 7 are at a magnification of 40,000. In both pressure-treated samples and the liquid control, amorphous and fibrous structures were observed, with amorphous material more prevalent than fibrous. FIG. 7A2 displays an amorphous structure from pressure-treated thermally-induced aggregates, which is representative of the dominant structure found for all three samples of rhIFN-γ. The observed structures and frequency of amorphous material relative to fibrous material in both pressure-treated aggregates and the liquid control were consistent. Additionally, there was no observed difference between the samples that were pressure-treated at 1 or 20 mg/mL for both the thermal- and guanidine hydrochloride-induced aggregates (comparison not shown). The fibrous network observed in the thermally-induced aggregate samples prior to pressure treatment was destroyed and a large proportion of the pressure-treated thermally-induced aggregate was amorphous. As well, the fibrous material that was observed in the pressure-treated guanidine hydrochloride-induced sample was not found in the guanidine hydrochloride-induced aggregate controls.

The fibrous structures seen for the pressure-treated aggregates and the liquid control were shorter in length and more varied in diameter than the fibrous structures observed in the thermally-induced aggregate controls. The lengths of the fibrous structures in the pressure-treated aggregates and the liquid control were generally 100 to 1000 nm in length and the diameters were typically ca. 12 nm but ranged up to ca. 25 nm. Some intertwined networks of fibrils were observed in all three sample sets and examples are given in FIGS. 7A3 and 7C2. It was concluded that the morphologies of the pressure-treated aggregates are indistinct from the control and that TEM sample preparation, which involves drying of the protein sample, induced structures consistent with both amorphous and fibrous aggregates.

Structural characterization after pressure treatment. Following the pressure-treatment, UV and FTIR absorbance spectra were collected and second derivative UV and FTIR spectra calculated for pressurized and control samples. The 10 and 20 mg/mL samples were diluted immediately after depressurization such that all UV analysis was conducted at 1 mg/mL rhIFN-γ. Due to concentration limitations of the technique, FTIR spectroscopy was performed only on the 10 and 20 mg/mL samples.

Figure 8A:
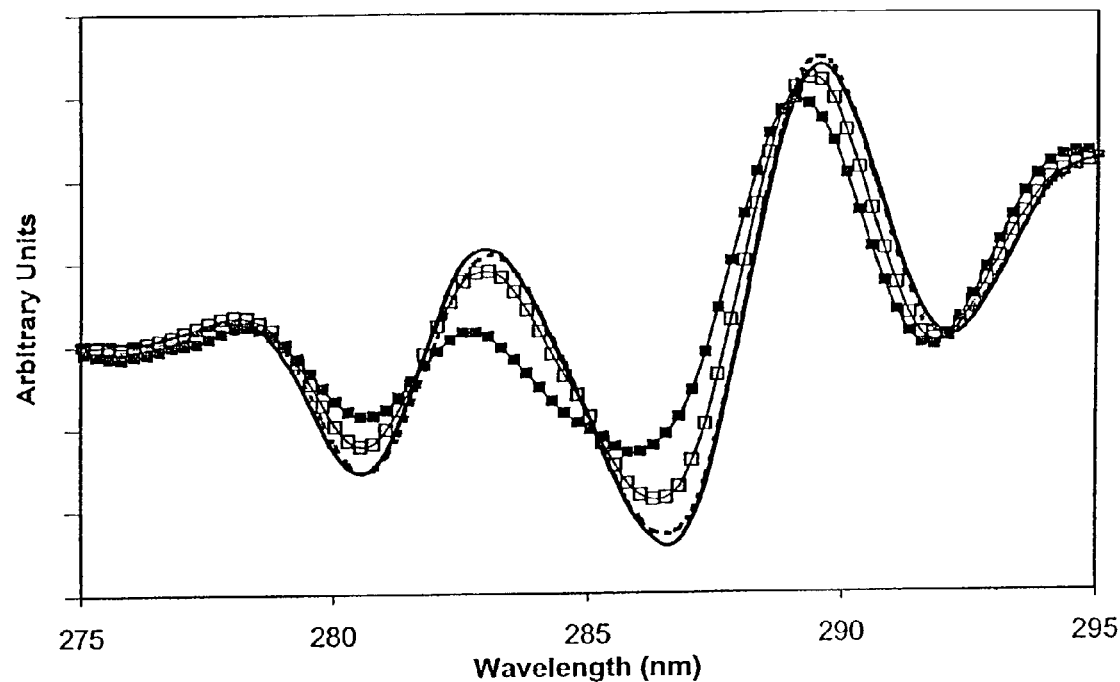
FIGS. 8A-8B: Second derivative UV spectra of (FIG. 8A) thermally-induced and (FIG. 8B) guanidine hydrochloride-induced pressure-treated aggregates. All spectra were collected at 0.1 MPa immediately after completion of the pressure refolding protocol. Refolding was performed at 20 mg/mL (solid symbols), 10 mg/mL (open symbols) and 1 mg/mL (dotted line) and spectra collected immediately after dilution to ca. 1 mg/mL. The spectrum of rhIFN-γ native control (solid line) is superimposed in both windows for reference.
Figure 8B:
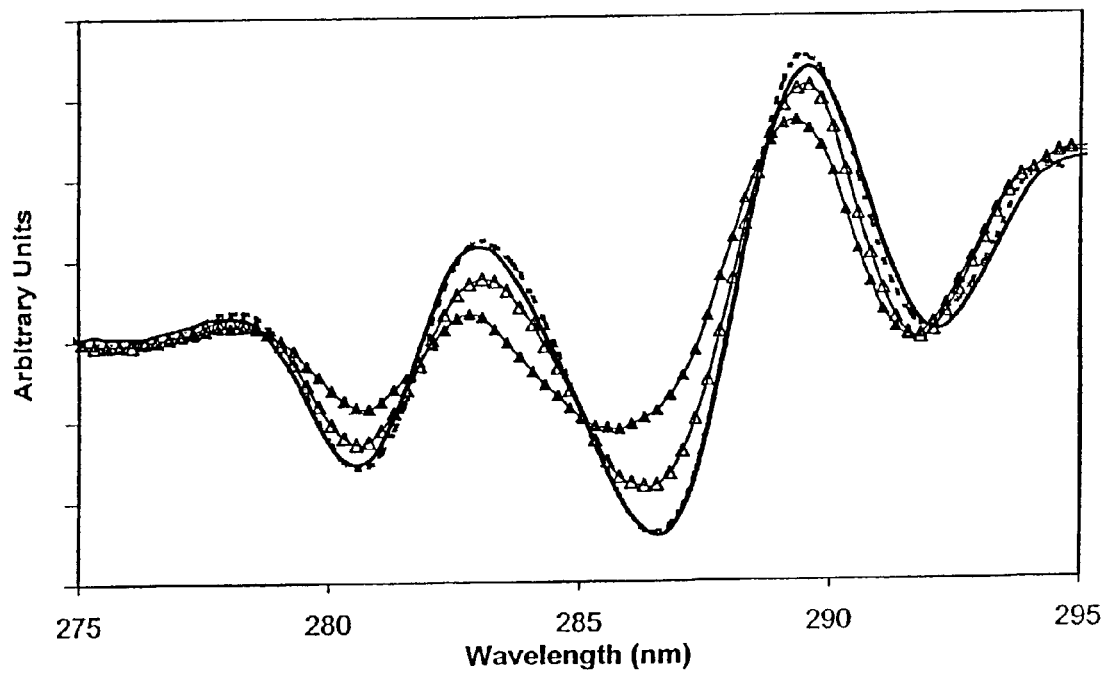

FIG. 8 is a plot of the second derivative UV spectra of (A) thermally-induced and (B) guanidine hydrochloride-induced, pressure-treated aggregates. Spectra were recorded at 0.1 MPa after the pressure-treatment protocol. For reference, the second derivative UV spectrum of native rhIFN-γ is superimposed on both windows of FIG. 8. The aggregate control spectra are omitted from FIG. 8 for clarity (see FIG. 4 for spectra of aggregates). The extent of recovery of the native second derivative UV spectrum is aggregate-form independent. But, the degree of recovery of the native second derivative UV spectrum is concentration dependent, with greater recovery of the native spectrum at lower protein concentrations. At 1 mg/mL, the pressure-treated aggregates recover nearly identical second derivative UV spectra as the native rhIFN-γ liquid control. Table 2 contains the summary of the percent recovery of the native spectrum measured by second derivative UV spectroscopy, using the ratio of the difference in heights of the extrema near 286 nm between the refolded and pressure-dissociated state relative to those of the native and pressure-dissociated states.

TABLE 2

Recovery of native spectral features for pressure-refolded aggregates of rhIFN-γ measured by second derivative UV and FTIR.

| | Thermally-induced | | Guanidine hydrochloride-induced | |
|---|---|---|---|---|
| Conc. during Refolding (mg/mL) | Percent recovery of Extremum near 286 nm UV | Area of Overlap of FTIR spectra | Percent recovery of Extremum near 286 nm UV | Area of Overlap of FTIR spectra |
| 1 | 97 | n/a | 99 | n/a |
| 10 | 89 | 88 | 88 | 90 |
| 20 | 79 | 69 | 76 | 69 |

Figure 9A:
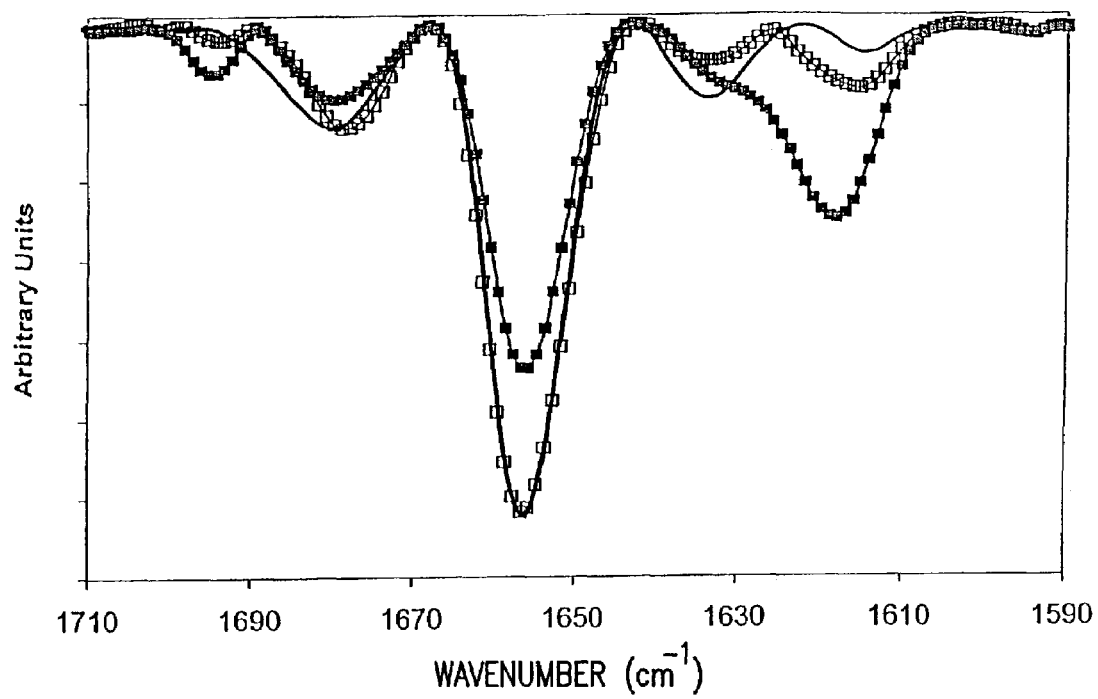
FIG. 9: Area normalized second derivative FTIR spectra of pressure-treated (FIG. 9A) thermally-induced and (FIG. 9B) guanidine hydrochloride-induced aggregates. All spectra were collected at 0.1 MPa within three hours of the completion of the pressure refolding protocol. FTIR spectra were recorded for refolding performed at 20 mg/mL (solid symbols), 10 mg/mL (open symbols). The spectrum of rhIFN-γ native control (solid line) is superimposed in both windows for reference.
Figure 9B:
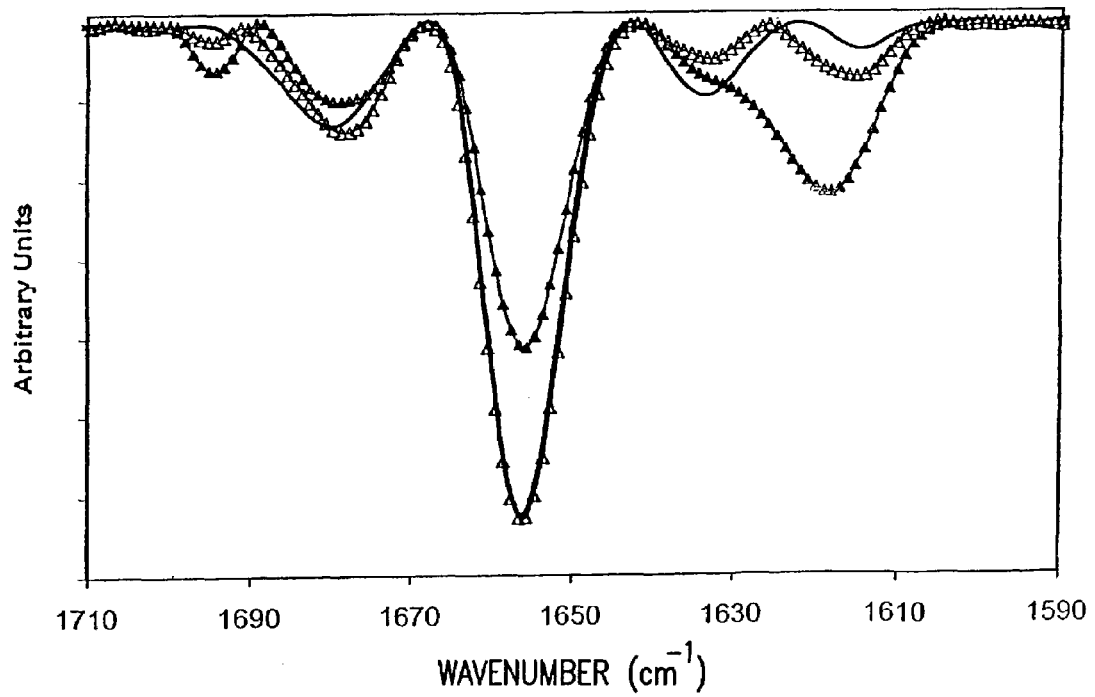

FIG. 9 is a plot of the area-normalized second derivative FTIR spectra of pressure-treated (FIG. 9A) thermally-induced and (FIG. 9B) guanidine hydrochloride-induced aggregates of rhIFN-γ for pressure-treatments conducted at 10 and 20 mg/mL. Due to the preparation and sample collection times associated with the FTIR technique, FTIR spectra were collected within three hours of depressurization. For comparative purposes, the second derivative FTIR spectrum of native rhIFN-γ is superimposed on both windows of FIG. 9. As was the case with the UV spectroscopic results, the recovery of native secondary structure, measured qualitatively by FTIR, is aggregate-form independent, as the second derivative FTIR spectra at 10 and 20 mg/mL are the same for both aggregate forms, respectively. However, the recovery of native-like secondary structure is dependent on the protein concentration during pressure treatment. There is substantial reduction in the intermolecular β-sheet bands near 1620 and 1695 $cm^{-1}$ with pressure treatment for both the 10 and 20 mg/mL samples. But, the reduction of these intermolecular β-sheet bands to levels observed in the native spectrum is nearly complete for the 10 mg/mL spectra, while significant bands are still present near 1620 and 1695 $cm^{-1}$ in each of the 20 mg/mL spectra. As measured by second derivative FTIR, the samples pressure-treated at 10 mg/mL recover all of the α-helix seen in the native structure (band near 1656 $cm^{-1}$). The recoveries of native secondary structure, as measured by area of overlap (Kendrick et al., 1996), are ca. 90 and 70% for the 10 and 20 mg/mL pressure-treatments, respectively. Table 2 compares the recovery of native structure by FTIR, as measured by area of overlap, with the recovery of native structure by second derivative UV spectroscopy. The percent recovery of native-like characteristics, as measured by UV and FTIR, are in reasonable agreement for both the 10 and 20 mg/mL pressure-treated samples, as the reproducibility of each method is ca. 5%.

Stability of pressure-treated aggregates: Physical characterization. After initial analysis following pressure treatment, the pressure-treated aggregate samples, aggregate controls and native controls were placed at 4° C. Two weeks after pressure treatment, the 10 and 20 mg/mL pressure-treated samples of both the thermally- and guanidine hydrochloride-induced aggregates had formed colorless, transparent gels, similar to the thermally-induced aggregates that were not pressure-treated. However, the viscosities of these samples (judged qualitatively) were noticeably lower than the viscosities observed for the thermally-induced aggregate controls. Qualitative time-dependent differences between the aggregates that were pressure-treated at 1 mg/mL were not apparent.

GEMMA and SEC were performed on the pressure-treated aggregates that had been diluted to 1 mg/mL in succinate buffer immediately after pressure treatment and subsequently stored for two weeks at 4° C. Results from GEMMA and SEC for the pressure-treated samples were compared to the liquid and aggregate controls. There were no observed effects, obtained either by GEMMA or SEC, with starting aggregate type or refolding protein concentration. As measured by GEMMA and SEC, the pressure-treated aggregates contained only two species, which were identified as monomer and dimer, and there were no detected higher-order aggregates in any of the pressure-treated aggregate samples or native controls. GEMMA analysis of the thermally-induced aggregate control showed a large (greater than 95% by mass) population of aggregates (FIG. 3) (again, GEMMA analysis was not performed on the guanidine hydrochloride-induced control).

A summary of the results between the native control and pressure-treated aggregates for GEMMA and SEC are presented in Tables 1A and 2B, respectively. Since there were no observed effects with starting aggregate type or refolding protein concentration, the data for the pressure-treated aggregates in Table 1 have been averaged over starting aggregate type and refolding protein concentration. The two peaks in the pressure-treated size distributions, as measured by GEMMA, were centered at 4.6 and 5.7 nm, which were larger in EM diameters than their respective counterparts in the distribution of the control (monomer and dimer). Additionally, by GEMMA, a greater mass percent monomer was observed in the refolded aggregates compared to the native control. By SEC, the elution time for the dimer was shorter for the pressure-treated aggregates than for the control, but there was no measured difference in elution time of the monomer. SEC observed no measurable differences in the mass percent monomer between the control and the pressure-treated aggregates. Since GEMMA and SEC data conflicted regarding an increase in mass percent monomer, the data do not support a conclusion of an increased mass percent monomer in the pressure-treated aggregate samples relative to the control.

For both the GEMMA and SEC data, MW estimations for monomer and dimer in the pressure-treated aggregate and native control samples were made from the calibration curves made with proteins of known MW and these MW estimations are presented in Table 1. The MW estimations for the monomer and dimer of the control samples were accurate by both GEMMA and SEC, as the known MW of rhIFN-γ monomer and dimer are 16.45 and 32.9 kD, respectively. The MW estimates for the dimer of the pressure-treated aggregate samples were larger by both GEMMA and SEC than the dimer MW estimate for the control samples. The increase in apparent MW of the dimer is believed to result from an improperly folded, expanded state dimer. The apparent MW for the monomer was larger by GEMMA, but unchanged by SEC, relative to the control.

Figure 10:
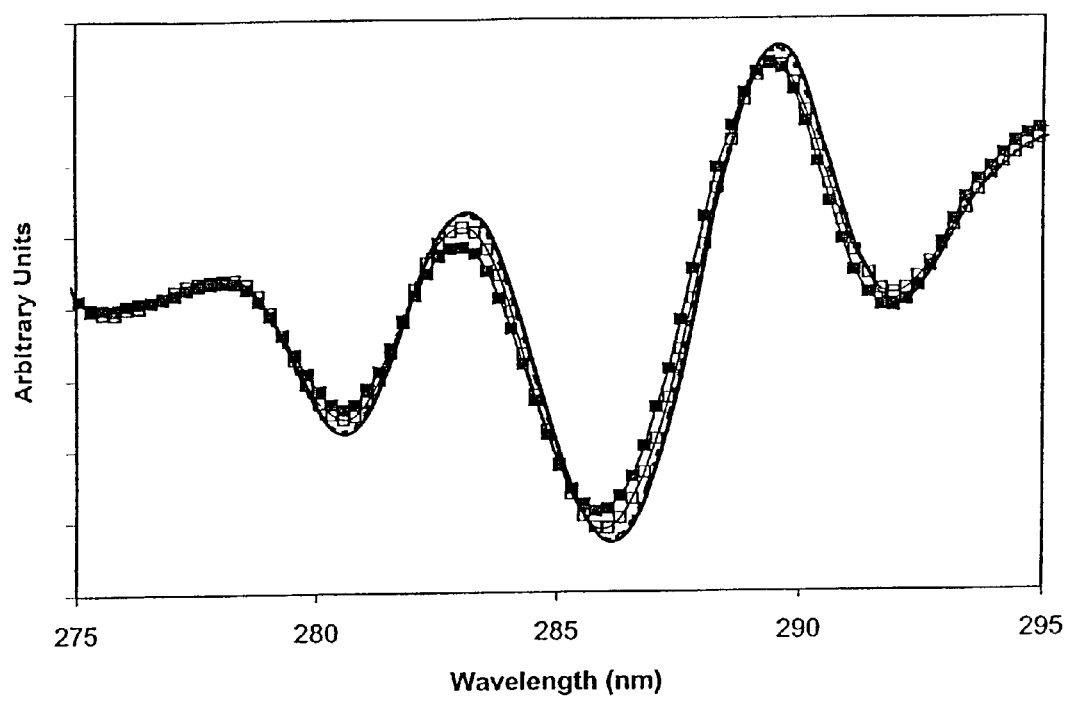
FIG. 10: Second derivative UV spectra of thermally-induced, pressure-treated aggregates after 2 weeks at 4° C., 0.1 MPa and 1 mg/mL. Refolding was performed at 20 mg/mL (solid symbols), 10 mg/mL (open symbols) and 1 mg/mL (dotted line) and samples immediately diluted to ca. 1 mg/mL. The spectrum of rhIFN-γ native control (solid line) is superimposed for reference.

Stability of pressure-treated aggregates: Structural characterization. Two weeks after the pressure refolding was performed, the samples that had been immediately diluted to 1 mg/mL upon depressurization were removed from storage at 4° C. and analyzed by UV. Concentration limitations prohibited analysis of these samples by FTIR. FIG. 10 is a plot of the second derivative UV spectra of thermally-induced, pressure-treated aggregates that were pressure-treated at 1, 10 and 20 mg/mL. For reference, the second derivative UV spectrum of native rhIFN-γ is superimposed on FIG. 10. The spectrum of the 1 mg/mL pressure-treated aggregate sample was the same as the spectrum taken immediately following the pressure treatment and showed essentially full recovery of native-like characteristics. However, the spectra of the 10 and 20 mg/mL pressure-treated aggregate samples were changed from the respective spectra taken immediately following pressure treatment (FIG. 8). Following storage at 1 mg/mL and 4° C. for two weeks, the recoveries of native structure, as measured by the height of the extremum near 286 nm, were 100, 97 and 94% for the 1, 10 and 20 mg/mL thermally-induced, pressure-treated aggregates, respectively. The recoveries of native structure for the 10 and 20 mg/mL thermally-induced, pressure-treated aggregates increased from 89 and 79% (Table 2) measured immediately after pressure treatment, respectively. As was the case immediately after pressure-treatment, the extent of recovery of the native second derivative UV spectrum two weeks after pressure treatment was aggregate-form independent. The second derivative UV spectra of guanidine hydrochloride-induced, pressure-treated aggregate samples are not presented, but the recoveries of native structure, as measured by the height of the extremum near 286 nm, were 100, 97 and 95% for the 1, 10 and 20 mg/mL samples, respectively. The recoveries of native structure, as measured by second derivative UV, after storage at 1 mg/mL and 4° C. show a decreasing trend with protein concentration during refolding, but the differences in recoveries are within the accuracy of the method.

Concentration dependence on recovery of native dimer. The recovery of native dimer from aggregates showed interesting protein concentration dependence. UV and FTIR spectroscopic data taken soon after the refolding protocol was completed indicate a strong concentration dependence on the extent of recovery. Additionally, the second derivative FTIR spectra taken after pressure treatment showed clear signs of aggregation, particularly for the samples refolded at 20 mg/mL (the presence of the intermolecular β-sheet bands at 1620 and 1695 cm$^{-1}$ in FIG. 9). Further, after two-weeks of storage at 4° C., the undiluted 10 and 20 mg/mL pressure-treated aggregate samples showed macroscopic evidence of aggregation by the visible increases in viscosities of these samples. However, the same pressure-treated samples, which had been diluted to 1 mg/mL immediately after pressure treatment, showed no signs of aggregates by GEMMA or SEC, were indistinct from the liquid control by TEM and showed nearly full recovery of native structure by UV analysis, regardless of protein concentration during refolding. To explain this interesting protein concentration dependence, it is necessary to understand the pressure effect on and the aggregation pathway of rhIFN-γ.

Hydrostatic pressure is known to dissociate oligomeric proteins (Gross & Jaenicke 1994; Silva & Weber 1993) and has been shown by the inventors to dissociate rhIFN-γ in the pressure region employed here for dissolution of aggregates. The in situ UV data collected during the refolding protocol indicated that after ca. one hour at 100 MPa refolding was essentially complete. The in situ UV data were collected at 1 mg/mL, but not at 10 and 20 mg/mL due to the absorbance limitation of the technique. Therefore, the refolding rate as a function of concentration at 100 MPa is not known. If the rate of refolding at 100 MPa is reduced at higher protein concentrations, then substantial monomer may have been present in the 10 and 20 mg/mL samples after the 1.5 hour refolding time at 100 MPa. The inventors showed second derivative UV spectra of the 10 and 20 mg/mL samples collected immediately after depressurization (FIG. 8) are consistent with increased monomer concentration. Further, it has been established by the inventors that rhIFN-γ aggregates via the monomer, and, therefore, presence of monomeric rhIFN-γ upon depressurization is expected to lead to aggregation. Thus, it is likely that the concentration dependence observed (immediately after the pressure treatment) in the second derivative UV spectra of pressure-treated aggregates (FIG. 8) reflects an increased monomer population at increased protein concentrations.

So, for the 10 and 20 mg/mL pressure-treated aggregate samples, why is aggregation observed in the undiluted samples and not in the samples that were diluted to 1 mg/mL rhIFN-γ? The answer lies in the relationship between protein aggregation and protein folding. Because protein aggregation proceeds through a folding intermediate, aggregation and folding are competitive processes (Betts et al., 1997; Clark et al., 1999; Fink, 1998). Protein refolding steps are generally first-order processes (Clark et al., 1999), but the inventors have determined that aggregation of rhIFN-γ in the absence of high electrolyte concentrations is second-order in protein concentration. If the rate-limiting step of rhIFN-γ folding is of lower order than two (e.g. first-order), then lower protein concentrations will favor refolding over aggregation. It is reasonable to envision the refolding kinetics of rhIFN-γ to be first-order when the intertwined nature of the dimer (Ealick et al., 1991) is considered. If the rate-limiting step in the acquisition of dimer is not the rate of collision of monomers, but the rate of assuming the correct conformation that allows the refolding to occur, then first-order kinetics would be observed. As well, lowering the temperature may contribute to the inhibition of aggregation and acquisition of dimer, as the aggregation reaction has a large activation energy, but the association reaction leading to dimer is relatively insensitive to temperature (Boteva et al., 1996). Thus, lower temperatures favor the refolding reaction over aggregation.

Example 3

Lysozyme Refolding

Pressure was generated using high-pressure nitrogen (40 MPa) connected to a 10-fold hydraulic intensifier (High Pressure Equipment Company, Erie, Pa.). One mg/ml suspensions of lysozyme aggregates in 50 mM Tris (pH 8.0, at 24° C.), varying amounts of GdnHCl, 2 mM DTT and GSSG at the desired final ratio (GSSG:GSH; an optimal ratio was 1:1) were prepared in heat-sealed bulbs of SAMCO® transfer pipets, sealed within a bag of water, and placed into a to a 2 liter cloverleaf reactor rated to 200 MPa and filled with oil. Samples were slowly pressurized (over 20 minutes) to final desired pressure to minimize pressurization-induced heating. Depressurization was conducted in 20 MPa increments, with each depressurization step requiring approximately 5 minutes. Samples were incubated at each intermediate pressure during depressurization for 15 minutes, yielding an overall depressurization rate of 1 MPa/minute (10 bar/minute). Thermal transients caused by pressure-induced heating were minimal (<2° C.) at this pressurization rate, as monitored by thermocouples mounted in the pressure vessel. Unless otherwise stated, all pressure experiments were performed at 24° C.

Example 4

Bikunin Refolding

Refolding studies were conducted on bikunin, a 170 amino acid protein with six disulfide bonds. This protein often forms an aggregate during fermentation. The aggregate is composed of non-native disulfide bonds and is an oligomer of four to eight monomers. Experiments were conducted to determine if high hydrostatic pressure (1000-3000 bar) could be used to refold these disulfide scrambled protein aggregates.

Aggregated bikunin was placed in sealed syringes and held under pressure at various reactor conditions. Pressure, pH, redox conditions, temperature and depressurization rate were all controlled. As a base case, the following conditions were used: 1 mg/ml sample of aggregated bikunin was held at 200 MPa, 25C., in 4 mM oxidized glutathione (GGSG), 2 mM dithiolthreitol (DTT) for 16 hours. The samples were then depressurized by 10 MPa every 30 minutes until a pressure of 100 MPa was reached. The samples were further depressurized 25 MPa every fifteen minutes until 0.1 MPa was reached. After pressurization, the samples were analyzed using size exclusion chromatography (SEC) to determine the refolding yield. A calibration curve was used to ensure that mass balance was maintained during experimentation. Samples were also sent to a secondary lab for analysis through reverse phase chromatography (RP) and activity assay. These secondary studies showed that SEC over-estimated the refolding yield by about 10% due to the presence of non-active monomeric proteins. SEC was still used as an optimization tool, however final refolding yields were confirmed with an activity assay.

A refolding yield of 45% +/−4% was obtained as measured by activity assay at the "base case" conditions described above. A rapid optimization of refolding conditions was obtained by varying solution conditions around the "base case" conditions. An unsophisticated algorithm was used; more sophisticated designed experiments well-known to industrial scientists would likely yield more optimal conditions with fewer experiments. However, even using the simple technique of varying redox conditions, temperature, pressure and depressurization rate separately around the base case conditions, a reasonable optimum was quickly found.

Figure 11:
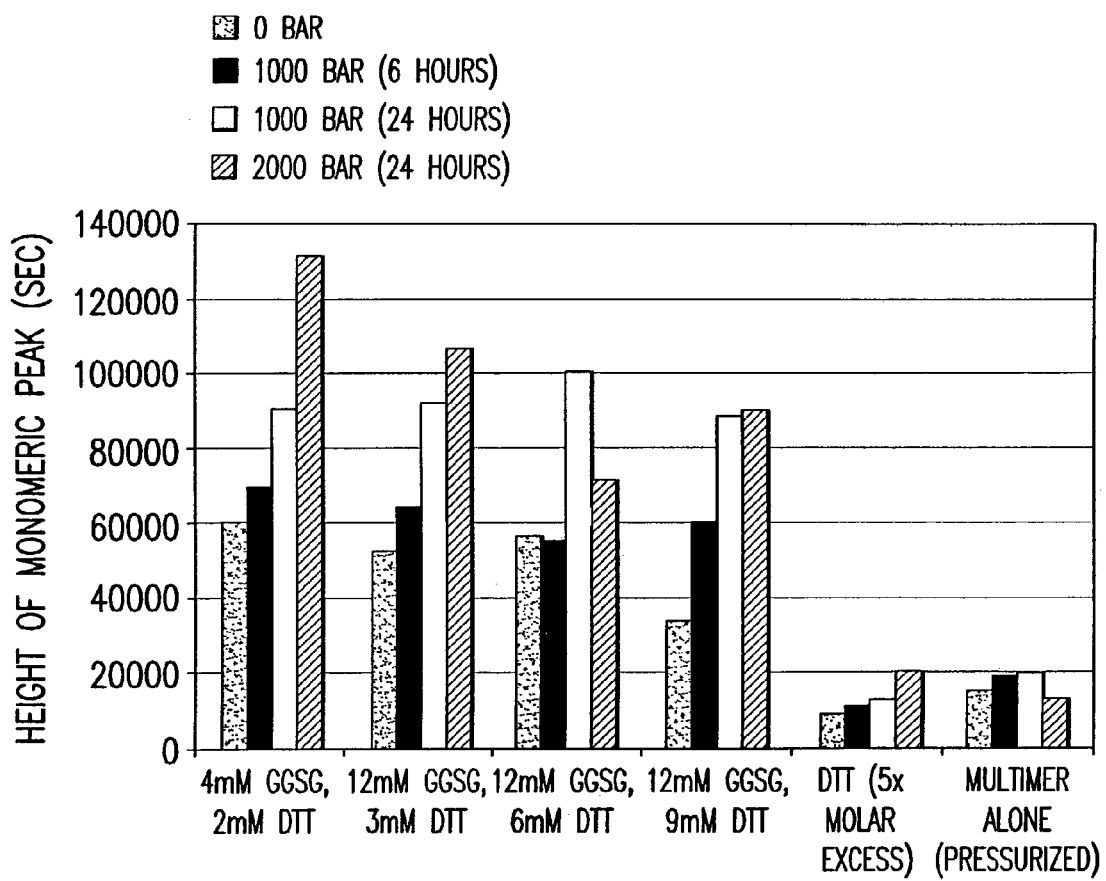
FIG. 11: Effect of redox conditions at various pressures on refolding yield. Conditions were 16 hours of refolding at 25° C., with 6 hours of depressurization. Maximum yield was obtained for samples in 4 mM GGSG, 2 mM DTT and held at 2000 bar.

Oxidized and reduced glutathione can be used to control the redox conditions within the refolding solution. These compounds are needed to break non-native disulfide bonds and reform native disulfides. Typically, optimum redox conditions exist when the total. glutathione concentration is between 6-16 mM, with ratios of reduced to oxidized glutathione specific to the system, often between 1 and 3. Samples were made with varying redox conditions and tested at three different pressure conditions to determine the effect on refolding yield. The ratio of the monomeric SEC peak to the aggregated SEC peak was used to measure the effectiveness of refolding. The results are shown in FIG. 11. For these studies, the most optimum case was found to be 4 mM oxidized glutathione, 2 mM DTT at 2000 bar.

The glutathione shuffling system was necessary to obtain any significant refolding yield, as would be expected for a protein aggregate containing non-native disulfide bonds. Pressure and DTT alone were not effective. Further optimization of the redox conditions could potentially be done; however, the yields obtained in 4 mM GGSG, 2 mM DTT at 2000 bar were adequate enough to determine the effects of the remaining refolding conditions.

Figure 12:
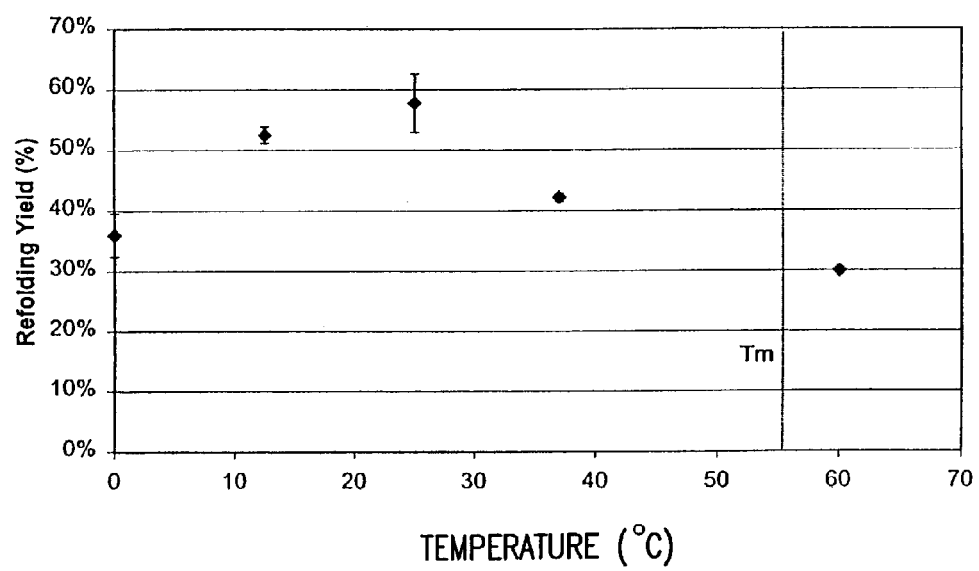
FIG. 12: Effect of temperature on refolding yield. Conditions were 2000 bar for 24 hours of refolding, 4 mM GGSG, 2 mM DTT, pH 7.2, with 8 hours of depressurization. Maximum yield was obtained when the refolding temperature was held at 25° C.

The effect of refolding temperature was evaluated. Samples were held at 12 hours at varying refolding temperatures, then brought to room temperature and held for an additional twelve hours. Pressures of 2000 bar and the previously optimized redox conditions were used. Refolding was found to be maximal at 25° C. These results are shown in FIG. 12.

Figure 13:
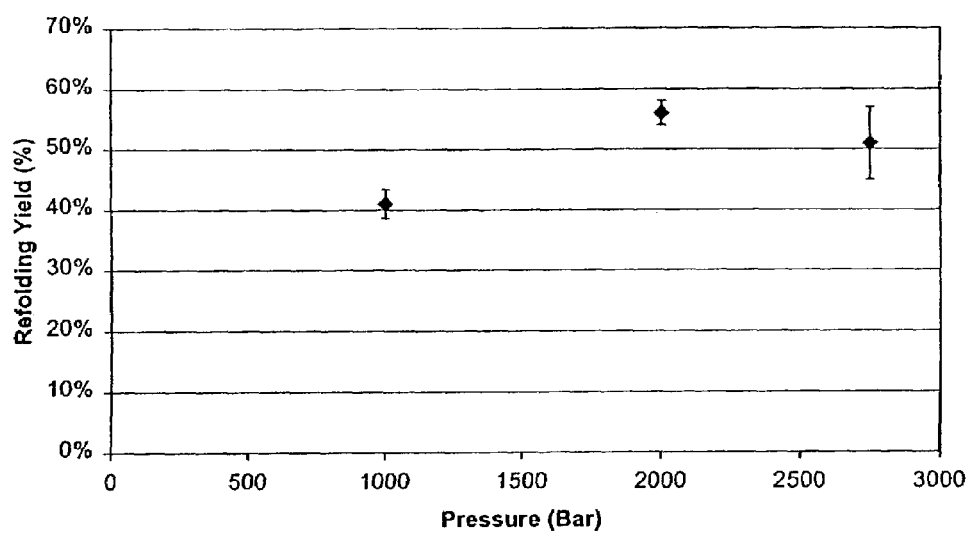
FIG. 13: Effect of pressure on refolding yield. Conditions were 16 hours of refolding, 4 mM GGSG, 2 mM DTT, 22° C., pH 7.2, with 8 hours of depressurization. Refolding yield was found to be a maximum at 2000 bar.

The effect of refolding pressure was evaluated. Samples were held at 16 hours at varying refolding pressures, and then slowly depressurized over an eight-hour period. The samples were held at room temperature, with the redox conditions previously used. 2000 bar was found to be the optimum refolding pressure, with refolding yield decreasing at both 1000 bar and 3000 bar. These results are shown in FIG. 13.

Protein monomer was subjected to rapid and slow depressurization rates to determine the impact of depressurization of protein yield. Samples were held at 2000 bar, 25° C., for 16 hours in the standard redox conditions (4 mM GGSG, 2 mM DTT). One set of samples was depressurized over a thirty second period. The second set of samples was depressurized according to the procedure described in the experimental methods (samples were depressurized by 10 MPa every 30 minutes until a pressure of 100 MPa was reached, then further depressurized 25 MPa every fifteen minutes until 0.1 MPa was reached). The samples that were depressurized slowly lost 21% +/−3% of the monomer to aggregates. This value was much lower than the 59% loss +/−16% when the sample was depressurized quickly. This study verified the need to use slow depressurization over a period of hours to ensure that the proteins maintain their native conformation.

Example 5 aVEGF Refolding

High pressure refolding studies were conducted on non-native dimeric aggregates of an antibody against human vascular endothelial growth factor (aVEGF), a full-length, disulfide binded, glycosylated, heterotetrameric antibody that undergoes irreversible dimerization during production in chinese hamster ovary (CHO) cell culture. Refolding studies were conducted to determine if high hydrostatic pressure could be used to obtain native aVEGF monomers. Additionally, experiments were run to determine the effect of temperature on refolding yield.

Experiments were conducted to determine the refolding yield of samples held at 2000 bar at three different temperatures. The experimental procedure is as follows: aVEGF (22% aggregate, 78% monomer) was diluted to a concentration of 1 mg/ml in 25 mM 2-(4-Morpholino)-ethane sulfonic acid (MES) buffer at pH 6.0. Each sample was made of 0.4 ml of the MES protein solution (1 mg/ml) loaded into a sealed syringe. The syringe is required to ensure proper pressure transfer to the sample. Three samples were created for each condition and placed into pressure vessels at room temperature. The samples were pressurized to 2000 bar and the pressure vessel temperature adjusted to 0° C., 25° C., or 50° C. The pressure was monitored during this time to maintain 2000 bar despite temperature changes. The samples were held at the desired temperature and pressure for sixteen hours, cooled or warmed to room temperature, and depressurized. Depressurization was done by 100 bar increments every thirty minutes, with drops of 250 bar every fifteen minutes once 1000 bar was reached. The samples were removed from the pressure vessels and stored at 4° C. for two days. Size exclusion chromatography (SEC) was used to determine the mass fractions of monomers and dimers.

Three samples were tested at 0° C., 25° C., and 50° C. and 2000 bar through the procedure described above. Refolding yield (RY %) was calculated from the SEC results using the following equation:

$$RY\ \% = \frac{M_f - M_i}{1 - M_i} * 100$$

where Mf=final monomer fraction and Mi=initial monomer fraction.

Figure 14:
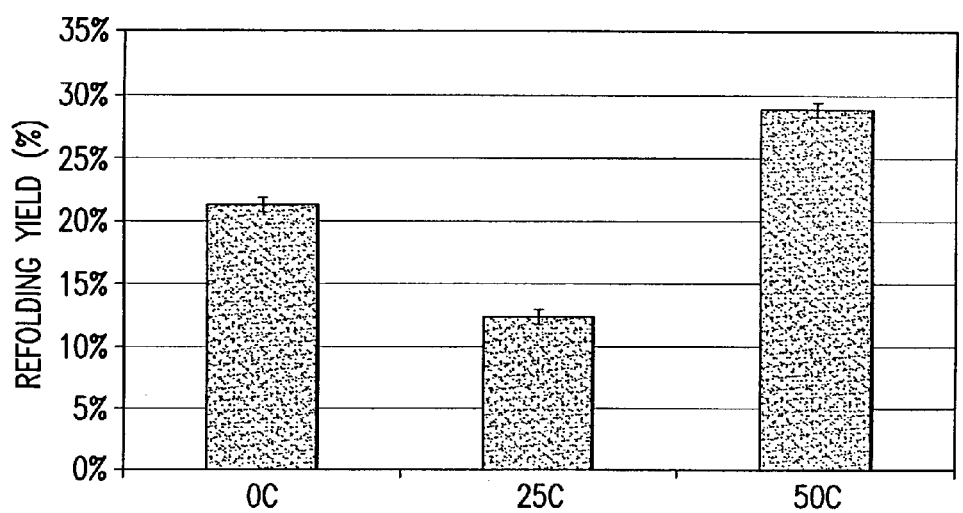
FIG. 14: Effect of temperature on a VEGF refolding. Conditions were 2000 bar for 16 hours, slow depressurization. A yield of 29% was achieved for samples held at 50° C. Error bars denote 95% confidence level.

Temperature was found to influence the refolding yield. These studies showed that a refolding yield of 29% (+/−1%) at 50° C. could be achieved. This is shown in FIG. 14.

Example 6

High Pressure Refolding of GCSF Inclusion Bodies

Concentrated, purified inclusion bodies supplied from Amgen, Inc. (Thousand Oaks, Calif.) were suspended in refolding buffer (50 mM Tris-HCl, 1 mM EDTA, 0.1% NaN$_3$) containing varying concentrations of guanidine hydrochloride (GdnHCl). Triplicate samples were pressurized to 2000 bar and incubated for 24 hours. Pressure was released by decreasing the vessel pressure in 200 bar increments. Samples were held at each incremental pressure for 15 minutes.

Figure 15:
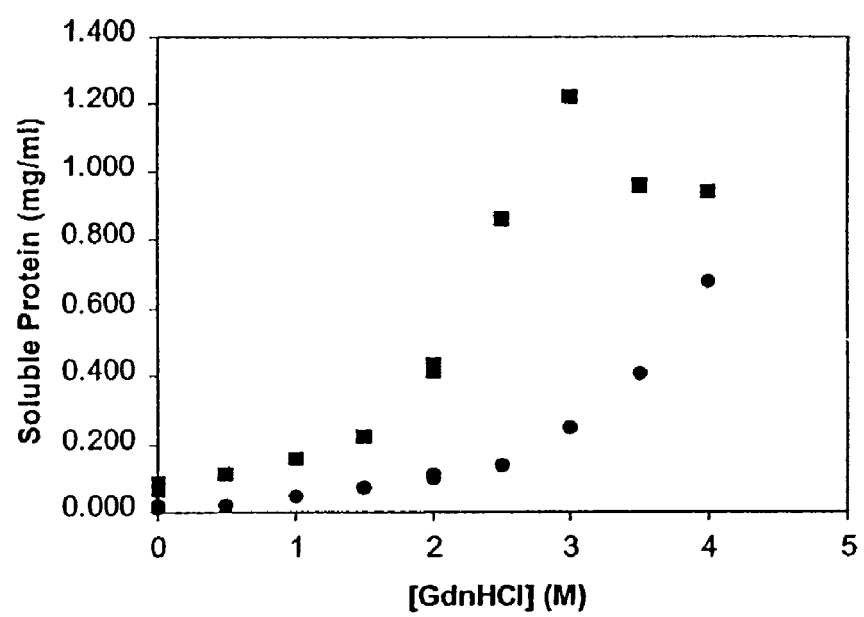
FIG. 15: Solubilized Protein from GCSF inclusion bodies: Circles (●) represent atmospheric samples. Squares (■) represent samples incubated at 2000 bar for 24 hours.

Upon complete depressurization, samples were centrifuged at 13,000 g for 15 minutes. The resulting supernatant was analyzed with the Pierce® TPA total protein assay. Bovine serum albumin (BSA) standards were used to calibrate the assay. The results are shown in FIG. 15.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XII. References

The following references, to the extent that they provide exemplary procedural or other details supplementary to those set forth herein, are specifically incorporated herein by reference.

U.S. Pat. No. 4,652,630
U.S. Pat. No. 4,659,568
U.S. Pat. No. 4,677,196
U.S. Pat. No. 4,766,224
U.S. Pat. No. 4,923,967
U.S. Pat. No. 4,929,700
U.S. Pat. No. 4,985,544
U.S. Pat. No. 5,023,323
U.S. Pat. No. 5,064,943
U.S. Pat. No. 5,077,392
U.S. Pat. No. 5,109,117
U.S. Pat. No. 5,162,507
U.S. Pat. No. 5,410,026
U.S. Pat. No. 5,593,865
U.S. Pat. No. 5,605,691
U.S. Pat. No. 5,708,148
U.S. Pat. No. 5,714,371
U.S. Pat. No. 5,728,804

Balestrieri, C., Colonna, G., Giovane, A., Irace, G., and Servillo, L. (1978). "2nd-Derivative Spectroscopy of Proteins—Method For Quantitative-Determination of Aromatic Amino-Acids in Proteins." *European Journal of Biochemistry*, 90(3), 433-440.

Benson, S. W. (1960). *The Foundations of Chemical Kinetics*, McGraw-Hill, New York.

Betts, S., Haase-Pettingell, C., and King, J. (1997). "Mutational effects on inclusion body formation." Advances in Protein Chemistry, Vol 50, Academic Press Inc, San Diego, 243-264.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F., and Pepys, M. B. (1997). "Instability, unfolding and aggregation of human lysozyme variants underlying amyloid fibrillogenesis." *Nature*, 385(6619), 787-793.

Carpenter, J. F., Kendrick, B. S., Chang, B. S., Manning, M. C., and Randolph, T. W. (1999). "Inhibition of stress-induced aggregation of protein therapeutics." Amyloid, Prions, and Other Protein Aggregates, R. Wetzel, ed., Academic Press Inc, San Diego, 236-255.

Carpenter, J. F., Pikal, M. J., Chang, B. S., and Randolph, T. W. (1997). "Rational design of stable lyophilized protein formulations: Some practical advice." *Pharmaceutical Research*, 14(8), 969-975.

Clark, E. D., Schwarz, E., and Rudolph, R. (1999). "Inhibition of aggregation side reactions during in vitro protein folding." Amyloid, Prions, and Other Protein Aggregates, Academic Press Inc, San Diego, 217-236.

Clark, E. D. B. (1998). "Refolding of recombinant proteins." *Current Opinion in Biotechnology*, 9(2), 157-163.

Dong, A., Prestrelski, S. J., Allison, S. D., and Carpenter, J. F. (1995). "Infrared spectroscopic studies of lyophilization- and temperature-induced protein aggregation." *Journal of Pharmaceutical Sciences*, 84(4), 415-24.

Ealick, S. E., Cook, W. J., Vijaykumar, S., Carson, M., Nagabhushan, T. L., Trotta, P. P., and Bugg, C. E. (1991). "3-Dimensional Structure of Recombinant Human Interferon-Gamma." *Science*, 252(5006), 698-702.

Fink, A. L. (1998). "Protein aggregation: folding aggregates, inclusion bodies and amyloid." *Folding & Design*, 3(1), R9-R23.

Foguel, D., Robinson, C. R., de Sousa, P. C., Silva, J. L., and Robinson, A. S. (1999). "Hydrostatic pressure rescues native protein from aggregates." *Biotechnology and Bioengineering*, 63(5), 552-558.

Gillmore, J. D., Hawkins, P. N., and Pepys, M. B. (1997). "Amyloidosis: A review of recent diagnostic and therapeutic developments." *British Journal of Haematology*, 99(2), 245-256.

Gorovits, B. M., and Horowitz, P. M. (1998). "High hydrostatic pressure can reverse aggregation of protein folding intermediates and facilitate acquisition of native structure." *Biochemistry*, 37(17), 6132-6135.

Gross, M., and Jaenicke, R. (1994). "Proteins Under Pressure—the Influence of High Hydrostatic—Pressure On Structure, Function and Assembly of Proteins and Protein Complexes." *European Journal of Biochemistry*, 221(2), 617-630.

Heremans, K., and Smeller, L. (1998). "Protein structure and dynamics at high pressure." *Biochimica Et Biophysica Acta-Protein Structure and Molecular Enzymology*, 1386 (2), 353-370.

Kauzman, W. (1959). "Some factors in the interpretation of protein denaturation." Advances in Protein Chemistry, Academic Press, San Diego, 1-63.

Kayed, R., Bemhagen, J., Greenfield, N., Sweimeh, K., Brunner, H., Voelter, W., and Kapurniotu, A. (1999). "Conformational transitions of islet amyloid polypeptide (IAPP) in amyloid formation in vitro." *Journal of Molecular Biology*, 287(4), 781-796.

Kendrick, B. S., Carpenter, J. F., Cleland, J. L., and Randolph, T. W. (1998a). "A transient expansion of the native state precedes aggregation of recombinant human interferon-gamma." *Proceedings of the National Academy of Sciences of the United States of America*, 95(24), 14142-14146.

Kendrick, B. S., Chang, B. S., Arakawa, T., Peterson, B., Randolph, T. W., Manning, M. C., and Carpenter, J. F. (1997). "Preferential exclusion of sucrose from recombinant interleukin-1 receptor antagonist: Role in restricted conformational mobility and compaction of native state." *Proceedings of the National Academy of Sciences of the United States of America*, 94(22), 11917-11922.

Kendrick, B. S., Cleland, J. L., Lam, X., Nguyen, T., Randolph, T. W., Manning, M. C., and Carpenter, J. F. (1998b). "Aggregation of recombinant human interferon gamma: Kinetics and structural transitions." *Journal of Pharmaceutical Sciences*, 87(9), 1069-1076.

Kim, Y. S., Wall, J. S., Meyer, J., Murphy, C., Randolph, T. W., Manning, M. C., Solomon, A., and Carpenter, J. F. (2000). "Thermodynamic modulation of light chain amyloid fibril formation." *Journal of Biological Chemistry*, 275(3), 1570-1574.

King, J., HaasePettingell, C., Robinson, A. S., Speed, M., and Mitraki, A. (1996). "Thermolabile folding intermediates: Inclusion body precursors and chaperonin substrates." *Faseb Journal*, 10(1), 57-66.

Laidler, K. J. (1965). *Chemical Kinetics*, McGraw-Hill, New York.

Lange, R., Frank, J., Saldana, J. L., and Balny, C. (1996). "Fourth derivative UV-spectroscopy of proteins under high pressure. 1. Factors affecting the fourth derivative spectrum of the aromatic amino acids." *European Biophysics Journal With Biophysics Letters*, 24(5), 277-283.

Leach, S. J. & Scheraga, H. A. (1960) *Journal of the American Chemical Society* 82, 4790-4792.

Lee, J. C., and Timasheff, S. N. (1981). "The stabilization of proteins by sucrose." *Journal of Biological Chemistry*, 256 (14), 7193-201.

Lilie, H., Schwarz, E., and Rudolph, R. (1998). "Advances in refolding of proteins produced in *E-coli*." *Current Opinion in Biotechnology*, 9(5), 497-501.

Liu, Y. F., and Bolen, D. W. (1995). "The Peptide Backbone Plays a Dominant Role in Protein Stabilization By Naturally-Occurring Osmolytes." *Biochemistry*, 34(39), 12884-12891.

Lumry, R., and Eyring, H. (1954). "Conformation changes of proteins." *Journal of physical Chemistry*, 58, 110-120.

NIST. (1998). "NIST webbook." http://webbook.NIST.gov.

Pace, C. N., Shirley, B. A., and Thomson, J. A. (1989). "Measuring the conformational stability of a protein." Protein structure: A practical approach, T. E. Creighton, ed., IRL Press, Oxford.

Prusiner, S. B. (1998). "Prions." *Proceedings of the National Academy of Sciences of the United States of America*, 95(23), 13363-13383.

Ragone, R., Colonna, G., Balestrieri, C., Servillo, L., and Irace, G. (1984). "Determination of Tyrosine Exposure in Proteins By 2nd-Derivative Spectroscopy." *Biochemistry*, 23(8), 1871-1875.

Sambrook et al., (1989), Molecular Cloning, Cold Spring Harbor Laboratory Press, Cold Spring Harbor, N.Y.

Scherzinger, E., Sittler, A., Schweiger, K., Heiser, V., Lurz, R., Hasenbank, R., Bates, G. P., Lehrach, H., and Wanker, E. E. (1999). "Self-assembly of polyglutamine-containing huntingtin fragments into amyloid-like fibrils: Implications for Huntington's disease pathology." *Proceedings of the National Academy of Sciences of the United States of America*, 96(8), 4604-4609.

Servillo, L., Colonna, G., Balestrieri, C., Ragone, R., and Irace, G. (1982). "Simultaneous Determination of Tyrosine and Tryptophan Residues in Proteins By 2nd-Derivative Spectroscopy." *Analytical Biochemistry*, 126(2), 251-257.

St. John, R. J., Carpenter, J. F., and Randolph, T. W. (1999). "High pressure fosters protein refolding from aggregates at high concentrations." *Proceedings of the National Academy of Sciences of the United States of America*, 96(23), 13029-13033.

Supran, M. K., Acton, J. C., Howell, A. J., and Saffle, R. L. (1971). "Surface tension of common aqueous and organic phases in food emulsions." *Journal of Milk and Food Technology*, 34(12), 584-585.

Timasheff, S. N. (1998). "Control of protein stability and reactions by weakly interacting cosolvents: The simplicity of the complicated." Advances in Protein Chemistry, Vol 51, Academic Press Inc. San Diego, 355-432.

Arakawa, T., Hsu, Y. R., and Yphantis, D. A. (1987). "Acid Unfolding and Self-Association of Recombinant *Escherichia-Coli* Derived Human Interferon-Gamma." *Biochemistry*, 26(17), 5428-5432.

Bam et al., (1998), *J. Pharm. Sci.* 87:1554-1559.

Boteva, R., Zlateva, T., DorovskaTaran, V., Visser, A., Tsanev, R., and Salvato, B. (1996). "Dissociation equilibrium of human recombinant interferon gamma." *Biochemistry*, 35(47), 14825-14830.

Kaufman, S. L., Skogen, J. W., Dorman, F. D., Zarrin, F., and Lewis, K. C. (1996). "Macromolecule analysis based on electrophoretic mobility in air: Globular proteins." *Analytical Chemistry*, 68(11), 1895-1904.

Kelly, J. W. (1996). "Alternative conformations of amyloidogenic proteins govern their behavior." *Current Opinion in Structural Biology*, 6(1), 11-17.

Kelly, J. W. (1998). "The environmental dependency of protein folding best explains prion and amyloid diseases." *Proceedings of the National Academy of Sciences of the United States of America*, 95(3), 930-932.

Kendrick, B. S., Dong, A. C., Allison, S. D., Manning, M. C., and Carpenter, J. F. (1996). "Quantitation of the area of overlap between second-derivative amide I infrared spectra to determine the structural similarity of a protein in different states." *Journal of Pharmaceutical Sciences*, 85(2), 155-158.

Mach, H., and Middaugh, C. R. (1994). "Simultaneous Monitoring of the Environment of Tryptophan, Tyrosine, and Phenylalanine Residues in Proteins By Near-Ultraviolet 2nd-Derivative Spectroscopy." *Analytical Biochemistry*, 222(2), 323-331.

Silva, J. L., Villasboas, M., Bonafe, C. F. S., and Meirelles, N. C. (1989). "Anomalous Pressure Dissociation of Large Protein Aggregates—Lack of Concentration—Dependence and Irreversibility At Extreme Degrees of Dissociation of Extracellular Hemoglobin." *Journal of Biological Chemistry*, 264(27), 15863-15868.

Silva, J. L., and Weber, G. (1993). "Pressure Stability of Proteins." *Annual Review of Physical Chemistry*, 44, 89-113.

Speed, M. A., Morshead, T., Wang, D. I. C., and King, J. (1997). "Conformation of P22 tailspike folding and aggregation intermediates probed by monoclonal antibodies." *Protein Science*, 6(1), 99-108.

Weber, G. (1993). "Pressure Dissociation of the Smaller Oligomers: Dimers and Tetramers." High Pressure Chemistry, Biochemistry and Materials Science, R. Winter and J. Jonas, eds., Kluwer Academic Press, Dordrecht, The Netherlands, 471-487.

Wetzel, R. (1994). "Mutations and Off-Pathway Aggregation of Proteins." *Trends in Biotechnology*, 12(5), 193-198.

Wetzel, R. (1999). "Amyloid, prions and other protein aggregates" Methods in Enzymology, J. N. Abelson and M. I. Simon, eds., Academic Press, San Diego, 820.

U.S. Ser. No. 60/244,080, filed Oct. 31, 2000.

The invention claimed is:

1. A method of producing biologically active disaggregated protein from protein aggregates comprising:
    (i) providing a protein aggregate;
    (ii) mixing said protein aggregate with a reducing agent in an amount sufficient to reduce disulfide bonds therein;
    (iii) subjecting the mixture of step (ii) to increased pressure of about 0.25 kbar to about 12 kbar, whereby said protein aggregate dissolves and/or disaggregates;
    (iv) dialyzing the mixture under pressure, whereby said reducing agent is removed and disulfide bonds reform; and
    (v) removing the dissolved and/or disaggregated protein from increased pressure, whereby said protein refolds such that biological activity is retained.

2. The method of claim 1, further comprising the step of agitating said protein aggregate and/or dissolved protein and/or disaggregated protein to enhance dissolution and/or disaggregation and/or refolding.

3. The method of claim 1, further comprising subjecting said protein aggregate, prior to refolding, to a temperature of about 30° C. to about 125° C.

4. The method of claim 3, wherein said method does not utilize a chaotropic agent.

5. The method of claim 1, wherein said reducing agent is dithiothreitol, glutathione, dithioerythritol, or β-mercaptoethanol.

6. The method of claim 1, wherein said increased pressure comprises about 500 atmospheres to about 10,000 atmospheres.

7. The method of claim 1, wherein steps (ii)-(v) are performed in about 3 hours to about 12 hours.

8. The method of claim 7, wherein steps (ii)-(v) are performed in about 6 hours.

9. The method of claim 1, wherein steps (ii) and (iii) are performed in the presence of a chaotropic agent, and said method further comprises the step of removing said chaotropic agent.

10. The method of claim 8, wherein said chaotropic agent is guanidine, guanidine sulfate, guanidine hydrochloride, urea, thiocyanate, sarcosyl, sodium dodecyl sulfate, or sodium octyl sulfate.

11. The method of claim 1, wherein said protein aggregate comprises inclusion bodies, soluble and insoluble precipitates, soluble non-native oligomers, gel, fibrils, films, filaments, protofibrils, amyloid deposits, plaques, or dispersed non-native intracellular oligomers.

12. A method of producing biologically active disaggregated protein from protein aggregates comprising:
    (i) providing a protein aggregate;
    (ii) subjecting the said protein aggregate to increased pressure of about 0.25 kbar to about 12 kbar, and high temperature of about 30° C. to about 125° C., whereby said protein aggregate dissolves and/or disaggregates; and
    (iii) removing the dissolved and/or disaggregated protein from increased pressure and high temperature,
whereby said protein refolds such that biological activity is retained.

13. The method of claim 12, wherein said method does not include use of a chaotropic agent.

14. The method of claim 12, further comprising the step of agitating said protein aggregate and/or dissolved protein and/or disaggregated protein to enhance dissolution and/or disaggregation and/or refolding.

15. The method of claim 12, further comprising mixing said protein aggregate with a reducing agent in an amount sufficient to reduce disulfide bonds therein.

16. The method of claim 15, further comprising dialyzing said mixture under pressure, whereby said reducing agent is removed and disulfide bonds reform.

17. The method of claim 15, further comprising removing said reducing agent by diafiltration or ultrafiltration.

18. The method of claim 15, further comprising negating the effect of said reducing agent by addition of an oxidizing agent.

19. The method of claim 15, wherein said reducing agent is dithiothreitol, glutathione, dithioerythritol, or β-mercaptoethanol.

20. The method of claim 12, wherein said increased pressure comprises about 0.5 kbar to about 10 kbar.

21. The method of claim 12, wherein steps (ii)-(iii) are performed in about 3 hours to about 12 hours.

22. The method of claim 21, wherein steps (ii)-(iii) are performed in about 6 hours.

23. The method of claim 12, wherein said protein aggregate comprises inclusion bodies, soluble and insoluble precipitates, soluble non-native oligomers, gel, fibrils, films, filaments, protofibrils, amyloid deposits, plaques, or dispersed non-native intracellular oligomers.

24. The method of claim 12, wherein steps (ii) and (iii) are performed in the presence of a chaotropic agent, and said method further comprises the step of removing said chaotropic agent.

25. The method of claim 24, wherein said chaotropic agent is guanidine, guanidine sulfate, guanidine hydrochloride, urea, thiocyanate, sarcosyl, sodium dodecyl sulfate, or sodium octyl sulfate.

26. A method of producing biologically active disaggregated protein from protein aggregates comprising:
(i) providing a protein aggregate;
(ii) mixing said protein aggregate with a reducing agent in an amount sufficient to reduce disulfide bonds therein;
(iii) subjecting the mixture of step (ii) to increased pressure of about 0.25 kbar to about 12 kbar, high temperature of about 30° C. to about 125° C., and agitation, whereby said protein aggregate dissolves and/or disaggregates;
(iv) removing or neutralizing said reducing agent, whereby disulfide bonds reform; and
(v) removing the dissolved and/or disaggregated protein from increased pressure and high temperature,
whereby said protein refolds such that biological activity is retained.

27. The method of claim 26, wherein said method does not include use of a chaotropic agent.

28. The method of claim 26, further comprising dialyzing said mixture under pressure, whereby said reducing agent is removed and disulfide bonds reform.

29. The method of claim 26, further comprising removing said reducing agent by diafiltration or ultrafiltration.

30. The method of claim 26, further comprising negating the effect of said reducing agent by addition of an oxidizing agent.

31. The method of claim 26, wherein said reducing agent is dithiothreitol, glutathione, dithioerythritol, or β-mercaptoethanol.

32. The method of claim 26, wherein said increased pressure comprises about 0.5 kbar to about 10 kbar.

33. The method of claim 26, wherein steps (ii)-(iii) are performed in about 1 hour to about 12 hours.

34. The method of claim 33, wherein steps (ii)-(iii) are performed in about 6 hours.

35. The method of claim 26, wherein said protein aggregate comprises inclusion bodies, soluble and insoluble precipitates, soluble non-native oligomers, gel, fibrils, films, filaments, protofibrils, amyloid deposits, plaques, or dispersed non-native intracellular oligomers.

36. The method of claim 26, wherein steps (ii) and (iii) are performed in the presence of a chaotropic agent, and said method further comprises the step of removing said chaotropic agent.

37. The method of claim 36, wherein said chaotropic agent is guanidine, guanidine sulfate, guanidine hydrochloride, urea, thiocyanate, sarcosyl, sodium dodecyl sulfate, or sodium octyl sulfate.

38. A method of refolding denatured protein comprising:
(i) providing a denatured protein composition;
(ii) mixing said protein composition with a reducing agent in an amount sufficient to reduce disulfide bonds therein;
(iii) subjecting the mixture of step (ii) to increased pressure of about 0.25 kbar to about 12 kbar;
(iv) dialyzing the mixture under pressure, whereby said reducing agent is removed and disulfide bonds reform; and
(v) removing the protein composition from increased pressure,
whereby said protein refolds such that biological activity is retained.

39. A method of refolding denatured protein comprising:
(i) providing a protein composition;
(ii) subjecting the said protein composition to increased pressure of about 0.25 kbar to about 12 kbar, and high temperature of about 30° C. to about 125° C.; and
(iii) removing the protein composition from increased pressure and high temperature,
whereby said protein refolds such that biological activity is retained.

40. A method of refolding denatured protein comprising:
(i) providing a protein composition;
(ii) mixing said protein composition with a reducing agent in amount sufficient to reduce disulfide bonds therein;
(iii) subjecting the mixture of step (ii) to increased pressure of about 0.25 kbar to about 12 kbar, high temperature of about 30° C. to about 125° C., and agitation;
(iv) removing or neutralizing said reducing agent, whereby disulfide bonds reform; and
(v) removing the protein composition from increased pressure and high temperature,
whereby said protein refolds such that biological activity is retained.

41. A method of rendering a protein aggregate susceptible to dissolution and/or disaggregation by detergents and/or increased temperature comprising subjecting said protein aggregate to high pressure of about 0.25 kbar to about 12 kbar in combination with one or more of detergents and/or increased temperature.

42. A method of producing biologically active disaggregated protein from protein aggregates comprising:
(i) providing a protein aggregate;
(ii) subjecting the mixture of step (i) to increased pressure of about 0.25 kbar to about 12 kbar, high temperature of about 30° C. to about 125° C. and agitation, whereby said protein aggregate dissolves and/or disaggregates;
(iii) altering the pH of the mixture of step (ii) by dialysis; and
(iv) removing the dissolved and/or disaggregated protein from increased pressure and high temperature,
whereby said protein refolds such that biological activity is retained.

* * * * *